(12) United States Patent
Ghosal

(10) Patent No.: US 8,894,993 B2
(45) Date of Patent: Nov. 25, 2014

(54) MITOCHONDRIA-TARGETED ANTIOXIDANTS

(75) Inventor: Shibnath Ghosal, Calcutta (IN)

(73) Assignees: Natreon Inc., New Brunswick, NJ (US); Indian Herbs Research & Supply Company, Ltd., Shardanagar (IN)

(*) Notice: Subject to any disclaimer, the term of this patent is extended or adjusted under 35 U.S.C. 154(b) by 1957 days.

(21) Appl. No.: 11/881,630

(22) Filed: Jul. 27, 2007

(65) Prior Publication Data

US 2008/0031862 A1 Feb. 7, 2008

Related U.S. Application Data

(60) Provisional application No. 60/835,520, filed on Aug. 4, 2006.

(51) Int. Cl.
| | | |
|---|---|---|
| *A61K 38/43* | (2006.01) |
| *A61K 38/54* | (2006.01) |
| *A61K 31/122* | (2006.01) |
| *A23L 1/30* | (2006.01) |
| *A23L 2/52* | (2006.01) |
| *A61K 8/34* | (2006.01) |
| *A61K 8/44* | (2006.01) |
| *A61K 31/37* | (2006.01) |
| *A61K 35/10* | (2006.01) |
| *A61Q 19/08* | (2006.01) |
| *A61Q 17/04* | (2006.01) |

(52) U.S. Cl.
CPC ............ *A61K 31/122* (2013.01); *A23L 1/30* (2013.01); *A23L 2/52* (2013.01); *A61K 8/347* (2013.01); *A61K 8/442* (2013.01); *A61K 31/37* (2013.01); *A61K 35/10* (2013.01); *A61Q 19/08* (2013.01); *A61Q 17/04* (2013.01)
USPC ......................... 424/94.1; 424/94.3

(58) Field of Classification Search
None
See application file for complete search history.

(56) References Cited

U.S. PATENT DOCUMENTS

| | | | | |
|---|---|---|---|---|
| 5,977,162 | A * | 11/1999 | Seidman | 514/440 |
| 6,440,436 | B1 * | 8/2002 | Ghosal | 424/401 |
| 6,558,712 | B1 * | 5/2003 | Ghosal | 424/725 |
| 6,869,612 | B2 * | 3/2005 | Ghosal | 424/401 |

* cited by examiner

*Primary Examiner* — Debbie K Ware
(74) *Attorney, Agent, or Firm* — Porzio, Bromberg & Newman, P.C.

(57) ABSTRACT

The present invention relates to a pharmaceutical or veterinary or nutritional or personal care composition comprising coenzyme $Q_{10}$ ($CoQ_{10}$), reduced $CoQ_{10}$, or mixtures thereof and oxygenated dibenzo-α-pyrone or an amino acyl ester thereof. The composition of the present invention is able to support and/or provide therapy to individuals at risk and/or under treatment for dysfunctions of energy metabolism, and specifically, for mitochondrial diseases.

6 Claims, 3 Drawing Sheets

(VII)

(VIII)

MITOCHONDRIA-TARGETED ANTIOXIDANTS

CROSS-REFERENCE TO RELATED PATENTS AND PATENT APPLICATIONS

This application claims the benefit of U.S. Provisional Application No. 60/835,520, filed on Aug. 4, 2006, the entirety of which is hereby incorporated by reference into this application.

This application is related to U.S. Pat. Nos. 6,869,612, 6,440,436 and 6,558,712 and pending U.S. Patent Application Publication No. 2005/0282781, the entire contents of which are hereby incorporated by reference in this application.

FIELD OF THE INVENTION

The present invention relates to compounds and methods for treatment and prevention of diseases, developmental delays, and symptoms related to mitochondrial dysfunction.

BACKGROUND OF THE INVENTION

Mitochondria are intracellular organelles responsible for energy metabolism. Consequently, mitochondrial dysfunction is damaging, particularly to neural and muscle tissues which have high energy demands.

Mitochondrial dysfunction is central to a number of human degenerative diseases, and can be due to primary defects in genes encoded by mitochondrial DNA, by mutations in nuclear encoded genes, or due to secondary consequences of other defects. Oxidative damage to the mitochondrion is a major factor in the pathophysiology of these diseases, because the mitochondrial respiratory chain is the major source of reactive oxygen species (ROS) within most human cells. These diseases include Parkinson's disease, Friedreich's Ataxia, Wilson's Disease, mtDNA diseases, diabetes, motor neuron disease and the non-specific loss of vigor associated with aging. Oxidative damage to mitochondria also contributes to the pathophysiology of inflammation and ischaemic-reperfusion injury in stroke, heart attack and during organ transplantation and surgery. Methods for treatment of diseases related to mitochondrial dysfunction are described in U.S. Pat. Nos. 6,956,028 and 6,511,966.

Mitochondrial anti-oxidant compounds are known and have been used as treatments, nutritional supplements and medium components. U.S. Pat. Nos. 6,984,636, 5,607,980, 5,472,698, 5,292,538, 5,536,645, 5,326,699, 6,562,869 and 6,479,069.

The predominant form of coenzyme Q in humans is coenzyme $Q_{10}$ ($CoQ_{10}$), which contains 10 isoprenoid units in the tail of the p-benzoquinone nucleus, whereas the predominant form in rodents is coenzyme $Q_9$ ($CoQ_9$). $CoQ_{10}$ is the precursor of $CoQ_9$, so administration of $CoQ_{10}$ to rats would provide $CoQ_9$ when systemically required. Coenzyme $Q_{10}$ (also known as ubiquinone) is present in all tissues and membranes in highly variable amounts. Various functions are attributed to coenzyme Q, depending on distribution and concentrations. It is a redox component; by interaction with NADH it is converted into the reduced form: coenzyme-$QH_2$ (e.g. ubiquinol), which plays the electron-carrier role in the mitochondrial electron transport chain. This electron carrier role was considered for a long time to be its only function. However, its broad distribution provides a clue to its additional cellular role,—claimed to be the only endogenously synthesized lipid soluble antioxidant (Ernster, L and Dallner, G, Biochemical, physiological and medical aspects of ubiquinone function. *Biochem. Biophys. Acta,* 1271:195-204, 1995). Coenzyme-$QH_2$ is a highly efficient antioxidant in preventing lipid, protein and DNA-oxidative damage. Coenzyme $QH_2$ is continuously regenerated from coenzyme $Q_{10}$ by intracellular reduction systems. In liposomes and in a mixture of lipoproteins, it was shown that $CoQ_{10}$ is preferentially utilized as an antioxidant when both this lipid and α-tocopherol were available. In some pathologic processes, when tissue concentration of $CoQ_{10}$ is decreased, it may be advantageous to supplement $CoQ_{10}$ by dietary supplement (Turunen M, Appelkvist E L, Sindelar P and Dallner G, Blood concentration of coenzyme $Q_{10}$ increases in rats when esterified forms are administered. *J. Nutr.,* 129:2113-2118, 1999). However, the effect of exogenous source of administration of $CoQ_{10}$ is difficult to interpret because in the absence of coenzyme-$QH_2$ ($CoQH_2$), the former can also be a pro-oxidant while acting as an electron acceptor that facilitates respiration.

From the mid-1970s, since $CoQ_{10}$ was synthetically prepared, it was used as a therapeutic agent in human physiological deficiencies, since $CoQ_{10}$ is an integral component of the electron transport chain in mitochondria of humans. U.S. Pat. Nos. 6,417,233, 6,867,024, and U.S. Patent Application Publication No. 2006/0024247. In the electron transport chain, $CoQ_{10}$ receives electrons from NADH, forms reduced $CoQ_{10}$ ($CoQH_2$) and passes the electron to cytochrome c, required for energy synthesis. After transfer of the electrons, reduced $CoQH_2$ is again oxidized to the quinone form ($CoQ_{10}$).

During physiological disorder, e.g. oxidative stress, the oxidation-reduction cycle of $CoQH_2 \square CoQ_{10}$ is impaired and $CoQ_{10}$ is randomly degraded to form polar aberrant metabolites. Oxidation of both $CoQH_2$ and $CoQ_{10}$ by systemic oxygen-centered free radicals produces intractable agglomerates. Oral intake or topical application of $CoQ_{10}$ alone, in such circumstances, is not able to completely restore the metabolic balance.

Accordingly, there is a need for compounds, compositions and methods that limit or prevent damage to organelles, cells and tissues initiated by mitochondrial dysfunction. The present invention fulfills the aforementioned needs and provides other related advantages.

SUMMARY OF THE INVENTION

The invention provides compositions that compensate for mitochondrial dysfunction, protect mitochondria from oxidative damage and boost energy.

In one aspect, the invention provides an isolated composition comprising: (a) Coenzyme $Q_{10}$ ($CoQ_{10}$), reduced $CoQ_{10}$, or mixtures thereof, and (b) oxygenated dibenzo-α-pyrone or an amino acyl ester thereof, wherein the composition is formulated as a cosmetic or personal care product.

Preferably, the inventive composition is in the form of a cream, ointment, suspension, powder, oil, lotion, oleo alcoholic lotion, fatty gel, oleo-alcoholic gel, solid stick, foam, emulsion, liquid dispersion, spray or aerosol.

Preferably, the dibenzo-α-pyrone of the inventive composition is 3,8-dihydroxy dibenzo-α-pyrone or 3-hydroxy dibenzo-α-pyrone. They can be obtained synthetically or by purification from natural sources. Preferably, the oxygenated dibenzo-α-pyrone or the amino acyl ester thereof is obtained from purified Shilajit and, more preferably, is further enriched with 3-hydroxy dibenzo-α-pyrone, 3,8-dihydroxy dibenzo-α-pyrone and their amino acyl esters. Preferably, the aminoacyl esters of oxygenated dibenzo-α-pyrone are glycine, arginine and equivalents. Preferably, the weight ratio of the benzoquinone to the oxygenated dibenzo-α-pyrone is in the range from 1:1 to 1:20.

It is also preferable that the composition of claim 1 comprises a solubilizer capable of solubilizing $CoQ_{10}$ in water. More preferably such composition additionally comprises an oligomeric oxygenated dibenzo-α-pyrone delivery system.

In another aspect, the inventive composition provides an isolated composition comprising: (a) Coenzyme $Q_{10}$ ($CoQ_{10}$), reduced $CoQ_{10}$, or mixtures thereof, and (b) oxygenated dibenzo-α-pyrone or an amino acyl ester thereof, wherein the composition is formulated as a food.

Preferably, the composition is present in the form of a beverage, candy, cookie, cereal, coffee powder, blended tea, nutritional bar, yogurt or pudding. Preferably, the composition is suitable for veterinary use in the form of wet food, dry food, or liquid formulation.

Preferably the dibenzo-α-pyrone is 3-hydroxy dibenzo-α-pyrone, 3,8-dihydroxy dibenzo-α-pyrone or their amino acyl esters. Preferably, the composition additionally comprises an oligomeric oxygenated dibenzo-α-pyrone delivery system.

In another aspect, the inventive composition provides an isolated composition comprising: (a) Coenzyme $Q_{10}$ ($CoQ_{10}$), reduced $CoQ_{10}$, or mixtures thereof, and (b) oxygenated dibenzo-α-pyrone or an amino acyl ester thereof, wherein the composition is formulated as a nutritional supplement in a granule, liquid or capsule form.

In yet another aspect, the invention is a method of treating a mitochondrial disorder comprising administering the inventive composition from the various aspects described above to a subject suffering from the mitochondrial disorder. Oral administration of the composition to an adult human in the amount of at least 5 mg/day is contemplated.

In another embodiment of the inventive method, the administered composition additionally contains a solubilizer to solubilize Coenzyme $Q_{10}$ in water. In yet another embodiment, the composition additionally comprises a carrier, delivery system, diluent or excipient that is acceptable for pharmaceutical, nutritional, cosmetic or veterinary usage. In one embodiment the carrier or delivery system comprises oligomeric oxygenated dibenzo-α-pyrones. In another embodiment, the carrier or delivery system is fulvic acid derived from 3,8-dihydroxy dibenzo-α-pyrone. In one embodiment the fulvic acid is obtained from purified shilajit.

DETAILED DESCRIPTION OF THE INVENTION

Figure 1:
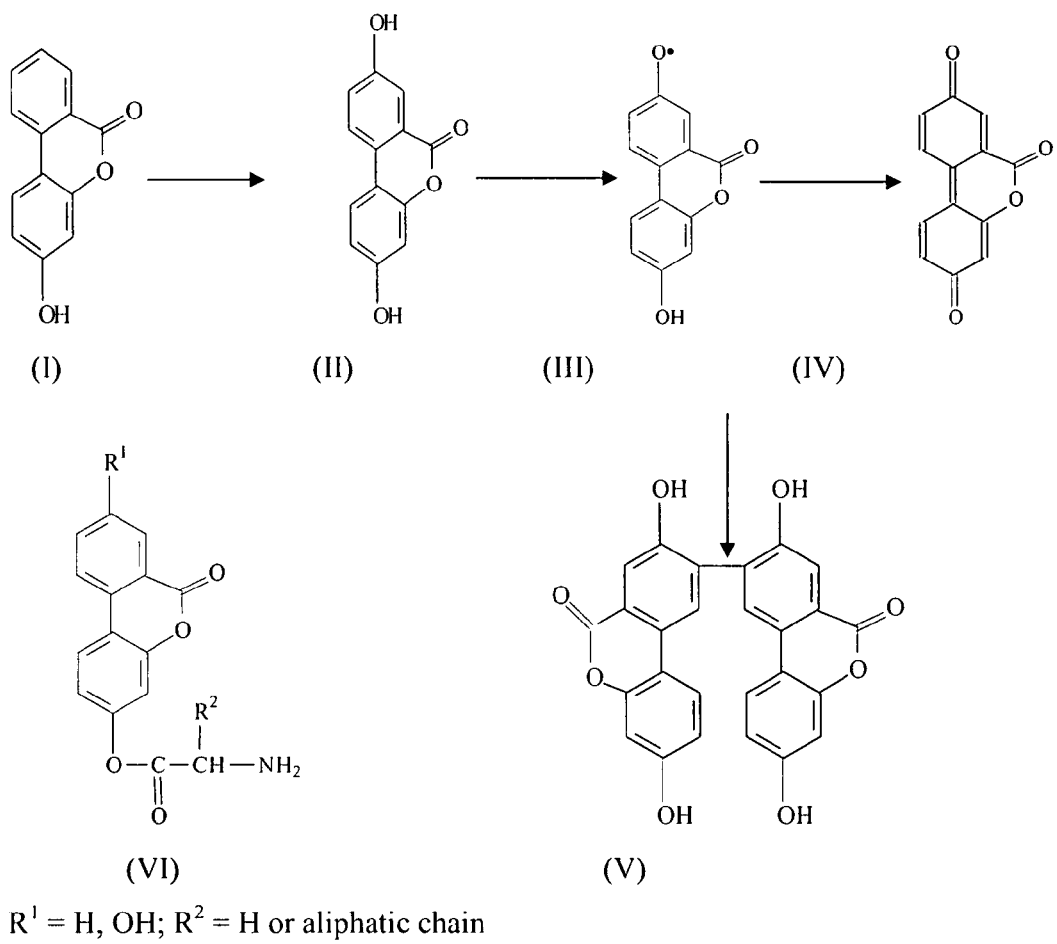
FIG. 1 Structures of dibenzo-α-pyrones and their oxidoreductive products.

Surprisingly, we have now observed, that, coenzyme $Q_{10}$ is not the only endogenously synthesized, lipid soluble antioxidant that functions and facilitates the electron transfer in the mitochondria (the power house of animal organisms). We have discovered that oxygenated dibenzo-α-pyrones (DBPs), are intimately associated with $CoQ_{10}$-$CoQH_2$, in all tissues and organelles. It has also been observed that in vivo concentration of DBPs (and equivalents) appreciably decrease with age and in pathological states. Hence, the role of DBPs, in different combination, has been investigated by targeting them to mitochondria, to alleviate the complications arising out of the deficiency of these cofactors.

Delivering $CoQ_{10}$ alone, as is the common practice till now (Matthews R T, Yang L, Browne S, Baik M and Beal M F, Coenzyme $Q_{10}$ administration increases brain mitochondrial concentrations and exerts neuroprotective effects. Proc. Natl. Acad. Sci., USA, 95:8892-8897, 1998) could not augment (present study) its systemic concentration as much as when $CoQ_{10}$ is administered along with DBP. Furthermore, we have developed a mitochondria-targeted DBP-coenzyme $Q_{10}$ delivery system, by using oligomeric DBPs obtained from Shilajit or other fossils, to make up the systemic deficiency of the two antioxidant electron transfer factors, to boost mitochondrial energy synthesis. Oxygenated dibenzo-α-pyrones along with ubiquinones, specifically, Coenzyme $Q_{10}$ are administered orally or topically to a mammal, including a human, for the purpose of compensating for mitochondrial dysfunction and for improving mitochondrial functions and energy boosting. The weight ratio of the lipid-soluble benzoquinone to the oxygenated dibenzo-α-pyrone is in the range from 1:1 to 1:20, as determined from animal studies. The term "treatment" as used herein in the context of treating a condition, pertains generally to treatment and therapy, whether of a human or an animal (e.g., in veterinary applications), in which some desired therapeutic effect is achieved, for example, the inhibition of the progress of the condition, and includes a reduction in the rate of progress, a halt in the progress, amelioration of the condition, or cure of the condition. Treatment as a prophylactic measure (i.e., prophylaxis) is also intended. The term "treatment" includes combination treatments and therapies, in which two or more treatments or therapies are combined, for example, sequentially or simultaneously.

The term "therapeutically-effective amount" as used herein, pertains to that amount of an active compound, or a material, composition or dosage form comprising an active compound, which is effective for producing some desired therapeutic effect, commensurate with a reasonable benefit/risk ratio.

The compound or pharmaceutical, veterinary, nutritional or personal care composition comprising the compound may be administered to a subject by any convenient route of administration, whether systemically/peripherally or topically (i.e., at the site of desired action). Administration can be effected in one dose, continuously or intermittently (e.g. in divided doses at appropriate intervals) throughout the course of treatment. Methods of determining the most effective means and dosage of administration are well known to those of skill in the art and will vary with the formulation used for therapy, the purpose of the therapy, the target cell(s) being treated, and the subject being treated. Single or multiple administrations can be carried out with the dose level and pattern being selected by the individual planning the treatment.

While it is possible for the active compound to be used (e.g., administered) alone, it is often preferable to present it as a formulation. The formulations may be prepared by any methods well known in the art of pharmacy. Such methods include the step of bringing into association the active compound with a carrier which constitutes one or more accessory ingredients. In general, the formulations are prepared by uniformly and intimately bringing into association the active compound with carriers (e.g. liquid carriers, finely divided solid carrier, etc.), and then shaping the product, if necessary.

Suitable carriers, diluents, excipients, etc. can be found in standard pharmaceutical texts. See, for example, Handbook for Pharmaceutical Additives, 2nd Edition (eds. M. Ash and I. Ash), 2001 (Synapse Information Resources, Inc., Endicott, N.Y., USA), Remington's Pharmaceutical Sciences, 18th edition, Mack Publishing Company, Easton, Pa., 1990; and Handbook of Pharmaceutical Excipients, 2nd edition, 1994, which are incorporated herein by reference.

The term "pharmaceutically or nutritionally or cosmetically acceptable" as used herein pertains to compounds, ingredients, materials, compositions, dosage forms, etc., which are, within the scope of sound scientific judgment, suitable for use in contact with the tissues of the subject in question (e.g. human) without excessive toxicity, irritation, allergic response, or other problem or complication, commensurate with a reasonable benefit/risk ratio. Each carrier, diluent, excipient, etc. must also be "acceptable" in the sense of being compatible with the other ingredients of the formulation.

The term "nutritional activity" as used herein pertains to nutritionally supplementing essential ingredients that are depleted in the body. As an individual ages, the body depletes certain essential ingredients, such as antioxidants, as Coenzyine $Q_{10}$, lipoic acid, acetyl carnithine, etc. Supplementation of depleted essential ingredients enables the body to function efficiently.

It will be appreciated by one of skill in the art that appropriate dosages of the active compounds, and compositions comprising the active compounds, can vary from patient to patient. Determining the optimal dosage will generally involve the balancing of the level of therapeutic benefit against any risk or deleterious side effects. The selected dosage level will depend on a variety of factors including, but not limited to, the activity of the particular compound, the route of administration, the time of administration, the rate of excretion of the compound, the duration of the treatment, other active ingredients, used in combination, the severity of the condition, and the species, sex, age, weight, condition, general health, and prior medical history of the patient. The amount of active compound and route of administration will ultimately be at the discretion of the physician, veterinarian, clinician, dermatologist or cosmetician, although generally the dosage will be selected to achieve local concentrations at the site of action which achieve the desired effect without causing substantial harmful or deleterious side-effects.

This invention delineates the role of DBPs, particularly 3,8-$(OH)_2$-DBP (Structure II, FIG. 1), in restoring homeostasis of the impaired human body. Amino acyl conjugates of oxygenated DBPs are also contemplated (cf structure VI, FIG. 1). Preferred amino acyl conjugates are glycine, arginine and equivalents. Equivalents can include a neutral amino acid, basic amino acid, serine, cysteine or methionine, among others. 3-OH-DBP (Structure I) is systemically converted into 3,8-$(OH)_2$-DBP when administered orally to animal organisms, hence biological function manifested by 3,8-$(OH)_2$-DBP would also represent the function of 3-OH-DBP. Purified shilajit contains DBPs (U.S. Pat. Nos. 6,869,612; 6,440,436) and oligomeric DBPs (U.S. Pat. No. 6,558,712). Use of the DBPs and oligomeric DBPs from purified shilajit are also contemplated as an embodiment of this invention. Purification of shilajit, as described in U.S. Pat. No. 6,869,612 includes a composition of the processed shilajit that contains fulvic acids and equivalents at greater than or equal to 60%, dibenzo-$\alpha$-pyrone chromoproteins at greater than or equal to 10% and total dibenzo-$\alpha$-pyrone at greater than or equal to 0.3%.

Pharmaceutical, Nutritional and Veterinary Formulations

The compositions herein may contain the inventive compound alone, or in combination with a carrier, delivery system, excipient or diluent that is acceptable for pharmaceutical, nutritional, cosmetic, or veterinary usage.

Suitable excipients are, in particular, fillers, such as sugars, for example, lactose, sucrose, mannitol or sorbitol; cellulose preparations and/or calcium phosphates, for example, tricalcium phosphate or calcium hydrogen phosphate; and binders, such as starches, for example, corn, wheat, rice or potato starch, gelatin, tragacanth, methyl cellulose and/or polyvinylpyrrolidone, and/or, if desired, disintegrants, such as the above mentioned starches, and also carboxymethyl starch, cross-linked polyvinylpyrrolidone, agar, alginic acid or a salt thereof such as sodium alginate, and/or flow regulators and lubricants, for example, silica, talc, stearic acid or salts thereof such as magnesium stearate or calcium stearate, and/or polyethylene glycol.

The compositions are prepared in dosage unit distributions such as tablets, coated tablets, hard or soft gelatin capsules, syrups, lotions, creams or sprays. These administrable forms can be prepared using known procedures, for example, by conventional mixing, granulating, tablet coating, dissolving or lyophilization processes. Thus, the active compositions can be prepared by combining the active ingredient with solid, liquid or emulsified carriers. Optionally, the processing by granulation or emulsification, can occur after the addition of suitable carriers, diluents or excipients.

Coated tablet cores can be provided with suitable coatings, which if appropriate are resistant to gastric juices, using, inter alia, concentrated sugar solutions which may contain gum arabic, talc, polyvinylpyrrolidone, polyethylene glycol and/or titanium dioxide, shellac solutions in suitable organic solvents or solvent mixtures or, for the preparation of coatings resistant to gastric juices, solutions of suitable cellulose preparations such as acetylcellulose phthalate or hydroxypropylmethylcellulose phthalate. Dyes or pigments can be added to the tablets or coated tablets, for example, to identify or indicate different doses of the active compound ingredient.

The orally administered vehicle in these formulations normally has no therapeutic activity and is nontoxic, but presents the active constituent to the body tissues in a form appropriate for absorption. In preparing formulations that are suitable for oral administration, one can use aqueous, water-miscible, or non-aqueous vehicles or carriers. Suitable absorption of the inventive compound normally will occur most rapidly and completely when the composition is presented as an aqueous solution. Modification of the vehicle with water-miscible liquids or substitution with water-immiscible liquids can affect the rate of absorption. The most important solvents in the miscible group are ethyl alcohol, polyethylene glycol, and propylene glycol.

Preferably, the vehicle of greatest value for the present inventive composition is water that meets the USP specification for water for injection. Generally, water of suitable quality for compounding will be prepared either by distillation or reverse osmosis to meet these USP specifications. The appropriate specifications for such formulations are given in Remington: The Science and Practice of Pharmacy, 19th Ed. at p. 1526-1528.

Another useful formulation is a reconstitutable composition which is a sterile solid packaged in a dry form. The reconstitutable dry solid is usually packaged in a sterile container with a butyl rubber closure to ensure the solid is kept at an optimal moisture range. A reconstitutable dry solid is formed by dry filling, spray drying, or freeze-drying methods. See Pharmaceutical Dosage Forms: Parenteral Medications, 1, p. 215-227.

Additional substances may be included in the compositions of this invention to improve or safeguard the quality of the composition. Thus, an added substance may affect solubility, provide for patient comfort, enhance the chemical stability, or protect against the growth of microorganisms. The composition may include an appropriate solubilizer, or substances which act as antioxidants, or a preservative. These substances will be present in an amount that is appropriate for their function, and will not adversely affect the action of the composition. Appropriate antioxidants are found in Remington (p. 1529). Examples of suitable antimicrobial agents include thimerosal, benzethonium chloride, benzalkonium chloride, triclosan, methyl p-hydroxybenzoate, propyl p-hydroxybenzoate, and parabens.

Preferred pharmaceutical or nutritional formulations are those suitable for oral administration to warm-blooded animals.

Other pharmaceutical or nutritional preparations suitable for oral administration are hard gelatin capsules and also soft gelatin capsules made from gelatin and a plasticizer such as glycerol or sorbitol. Hard capsules may include the inventive compound in admixture with fillers such as lactose, binders such as starches, and/or lubricants such as talc or magnesium stearate, and if desired, stabilizers. In soft capsules, the inventive compound is preferably dissolved or suspended in a suitable liquid, such as fatty oil, paraffin oil or a liquid polyethylene glycol, to which a stabilizer can be added.

Antioxidants relevant to mitochondria dysfunction are also part of this inventive composition, which include but are not limited to natural tocopherols, acetyl carnitine, lipoic acid, ascorbic acid, idebenone, N-acetyl cysteine, superoxide dismutase, catalase, glutathione peroxidase, etc.

The compositions of the present invention can include one or more solubilizers, i.e., additives to increase the solubility of $CoQ_{10}$ or other components in the inventive compositions. Suitable solubilizers for use in the compositions of the present invention include:

alcohols and polyols, such as ethanol, isopropanol, butanol, benzyl alcohol, ethylene glycol, propylene glycol, butanediols and isomers thereof, glycerol, pentaerythritol, sorbitol, mannitol, transcutol, dimethyl isosorbide, polyethylene glycol, polypropylene glycol, polyvinylalcohol, hydroxypropylmethyl cellulose and other cellulose derivatives, cyclodextrins and cyclodextrin derivatives;

ethers of polyethylene glycols having an average molecular weight of about 200 to about 6000, such as tetrahydrofurfuryl alcohol PEG ether (glycofurol, available commercially from BASF under the trade name Tetraglycol) or methoxy PEG (Union Carbide);

amides, such as 2-pyrrolidone, 2-piperidone, ε-caprolactam, N-alkylpyrrolidone, N-hydroxyalkylpyrrolidone, N-alkylpiperidone, N-alkylcaprolactam, dimethylacetamide, and polyvinylpyrrolidone;

esters, such as ethyl propionate, tributylcitrate, acetyl triethylcitrate, acetyl tributyl citrate, triethylcitrate, ethyl oleate, ethyl caprylate, ethyl butyrate, triacetin, propylene glycol monoacetate, propylene glycol diacetate, ε-caprolactone and isomers thereof, δ-valerolactone and isomers thereof, β-butyrolactone and isomers thereof; and other solubilizers known in the art, such as dimethyl acetamide, dimethyl isosorbide (Arlasolve DMI (ICI)), N-methylpyrrolidones (Pharmasolve (ISP)), monooctanoin, diethylene glycol monoethyl ether (available from Gattefosse under the trade name Transcutol), and water.

Mixtures of solubilizers are also within the scope of the invention. Except as indicated, these compounds are readily available from standard commercial sources.

Preferred solubilizers include triacetin, triethylcitrate, ethyl oleate, ethyl caprylate, dimethylacetamide, N-methylpyrrolidone, N-hydroxyethylpyrrolidone, polyvinylpyrrolidone, hydroxypropylmethyl cellulose, hydroxypropyl cyclodextrins, ethanol, polyethylene glycol 200-600, glycofurol, transcutol, propylene glycol, and dimethyl isosorbide. Particularly preferred solubilizers include sorbitol, glycerol, triacetin, ethyl alcohol, PEG-400, glycofurol and propylene glycol.

The amount of solubilizer that can be included in compositions of the present invention is not particularly limited. Of course, when such compositions are ultimately administered to a patient, the amount of a given solubilizer is limited to a bioacceptable amount, which is readily determined by one of skill in the art. In some circumstances, it may be advantageous to include amounts of solubilizers far in excess of bioacceptable amounts, for example, to maximize the concentration of active ingredient, with excess solubilizer removed prior to providing the composition to a patient using conventional techniques, such as distillation or evaporation.

Personal care or cosmetic compositions of this invention may contain dispersing agents, emulsifiers or thickening agents to assist in applying a uniform layer of the active compounds. Suitable dispersing agents for the composition include those useful for dispersing organic or inorganic sunscreen agents in either a water phase, oil phase, or part of an emulsion, including, for example, chitosan.

Suitable emulsifiers include agents such as, for example, glycerol stearate, stearyl alcohol, cetyl alcohol, dimethicone copolyol phosphate, hexadecyl-D-glucoside, octadecyl-D-glucoside, etc.

Suitable thickening agents include carbomers, acrylate/acrylonitrile copolymers, xanthan gum and combinations of these. The carbomer thickeners include the crosslinked CARBOPOLOR acrylic polymers from B.F. Goodrich. The amount of thickener within the composition, for example, on a solids basis without water, may range from about 0.001 to about 5%, preferably from 0.01 to about 1% and optimally from about 0.1 to about 0.5% by weight.

Minor optional adjunct ingredients for the compositions may include preservatives, waterproofing agents, fragrances, anti-foam agents, plant extracts (Aloe vera, witch hazel, cucumber, etc) opacifiers, skin conditioning agents and colorants, each in amounts effective to accomplish their respective functions.

The compositions may optionally contain an ingredient which enhances the waterproof properties such as, compounds that form a polymeric film, such as dimethicone copolyol phosphate, diusostearoyl trimethyolpropane siloxysilicate, chitosan, dimethicone, polyethylene, polyvinylpyrrolidone (PVP), polyvinylpyrrolidone/vinylacetate, PVP/Eiconsene copolymer and adipic acids/diethylene glycol/glycerine crosspolymer etc. Waterproofing agents may be present at levels of from about 0.01 to about 10% by weight.

The compositions may also optionally contain one or more skin conditioning agents. These include humectants, exfoliants and emollients.

Humectants are polyhydric alcohols intended for moisturizing, reducing scaling and stimulating the removal of built scale from the skin. Typically polyhydric alcohols include polyalkylene glycols and more preferably alkylene polyols and their derivatives. Illustrative are propylene glycol, dipropylene glycol, polypropylene glycol, polyethylene glycol, sorbitol, 2-pyrrolidone-5-carboxylate, hydroxypropyl sorbitol, hexylene glycol, ethoxydiglycol 1,3-butylene glycol, 1,2, 6-hexanetriol, glycerin, ethoxylated glycerin, propoxylated glycerin and mixtures thereof. Most preferably the humectant is glycerin. Amounts of humectant can range anywhere from 1 to 30%, preferably from 2 to 20% and optimally from about 5 to 10% by weight of the composition.

The exfoliants suitable for use in the present invention may be selected from alpha-hydroxy carboxylic acids, beta hydroxycarboxylic acids and salts of these acids. Most preferred are glycolic, lactic and salicylic acids and their alkali, metal or ammonium salts.

Suitable emollients include those agents known for softening the skin or hair which may be selected from hydrocarbons, fatty acids, fatty alcohols and esters. Petrolatum is a common hydrocarbon type of emollient conditioning agent. Other hydrocarbons that may be employed include alkyl benzoate, mineral oil, polyolefins such as polydecene, and paraffins, such as isohexadecane. Fatty acids and alcohols typically have from about 10 to 30 carbon atoms. Illustrative are myristic, isostearic, hydroxystearic, oleic, linoleic, ricinoleic, behenic and eruicic acids and alcohols. Oily ester emollients may be those selected from one or more of the following, triglyceride esters, acetoglyceride esters, ethoxylated glycerides, alkyl esters of fatty acids, ether esters, polyhydric alcohol esters and wax esters. Additional emollients or hydrophobic agents include $C_{12}$ to $C_{15}$ alkyl benzoate, dioctyladipate, octyl stearate, octyldodecanol, hexyl laurate, octyldodecyl neopentanoate, cyclomethicone, dicapryl ether, dimethicone, phenyl trimethicone, isopropyl myristate, capriylic/capric glycerides, propylene glycol dicaprylate/dicaprate and decyl oleate, isopropyl citrate, diisopropyl adipate, ethylhexyl neopentanoate, isopropyl laurate, hexyl laurate, $C_{12-15}$ alkyl benzoate, ethylhexyl palmitate, octyldodecyl neopentatnoate, ethylhexyl state etc.

Examples of esters of long-chain fatty acids, for example, include: long-chain fatty acid esters of retinol; long-chain fatty acid ester of ascorbic acid; long-chain fatty acid ester of glycerol; etc. The long-chain fatty acid ester of retinol can be selected from the group consisting of retinyl palmitate, retinyl myristate, and retinyl stearate. Most preferably, the retinyl ester is retinyl palmitate. Preferably, the retinyl ester comprises from about 0.05% to about 0.15% of a skin cream composition. The long-chain fatty acid ester of ascorbate can be selected from the group consisting of ascorbyl myristate, ascorbyl palmitate, and ascorbyl stearate. Preferably, the ascorbic acid ester is ascorbyl palmitate. Preferably, the ascorbic acid ester comprises from about 0.01% to about 0.02 to 0.03% of the composition.

The long-chain fatty acid ester of glycerol can be selected from the group consisting of glyceryl stearate, glyceryl palmitate, and glyceryl arachidate. Preferably, the ester of glycerol is glyceryl stearate. Preferably, the glyceryl stearate comprises from 0.5% to about 0.7% of the composition.

Examples of short or long chain alcohols, for example, include: hexyl (chain-length, C-6), caprylyl (C-8), decyl (C-10), lauryl (C-12), myristyl (C-14), cetyl (C-16), stearyl (C-18), arachidyl (C-20), behenyl alcohols (C-22).

The personal care or cosmetic compositions may optionally contain one or more inorganic sunscreen agents as discussed above including micro fine surface treated titanium dioxide and micro fine untreated and surface treated zinc oxide. Titanium dioxide in the compositions preferably has a mean primary particle size of between 5 and 150 nm and preferably from 10 to 100 nm. Titanium oxide may have anatase, rutile or amorphous structure. The zinc oxide in the sunscreen compositions preferably has a mean primary particle size of between 5 nm and 150 nm, preferably between 10 nm and 100 nm.

Antioxidants relevant to mitochondria dysfunction include but are not limited to natural tocopherols, acetyl carnitine, lipoic acid, idebenone, N-acetyl cysteine, superoxide dismutase, catalase, glutathione peroxidase are also included in the personal care or cosmetics applications. Although not preferred, the compositions may contain an additional conventional antioxidant. Examples of suitable antioxidants which provide stability include p-hydroxybenzoic acid and its derivatives (ethylisobutyl, glyceryl esters of p-hydroxybenzoic acid); salicylates (octylamyl, phenyl, benzyl menthyl, glycerol and dipropyleneglycol esters); coumarin derivatives; flavones; hydroxy or methoxy substituted benzophenones; uric or tannic acid and its derivatives; and benzophenones. Also, the compositions may contain natural antioxidants, such as, Emblica antioxidant, Pine antioxidant, Grape antioxidant, Green tea antioxidant and others.

The personal care and cosmetics formulations can be in the form of creams, ointments, suspensions, powders, oil, lotions, oleo alcoholic lotions, fatty gels, oleo-alcoholic gels and lotions, solid sticks, foams, emulsions, liquid dispersions, sprays and aerosols. More specific forms include: lotions, lipsticks, foundations, makeup, loose or press powder, eye blush, eye shadow, shampoo, conditioner and nail lacquer.

EXPERIMENTAL

Example 1

Chemical Synthesis of 3-hydroxydibenzo-α-pyrone

2-Bromobenzoic acid (5.8 grams), resorcinol (5.5 grams) and sodium hydroxide (2 grams) in water (25 ml) were heated under reflux for 10 minutes. After the addition of aqueous copper sulphate (5%, 10 ml), the mixture was refluxed again for 10 min. At the completion of the heating, 3-hydroxy-dibenzo-alpha-pyrone precipitated as a cream colored amorphous powder (8.7 grams). It was crystallized from ethyl acetate as micro-crystalline solid, m.p. 230-232° C.

Example 2

Chemical Synthesis of 3,8-dihydroxydibenzo-α-pyrone

A mixture of 2-bromo-5-methoxybenzoic acid (5.6 grams), resorcinol (5.5 grams) and sodium hydroxide (2.2 grams) in water (25 ml) was heated under reflux for 30 minutes. After the addition of copper sulphate (5% aqueous solution, 10 ml), the mixture was refluxed again for 10 min when 3-hydroxy-8-methoxydibenzo-alpha-pyrone (3.7 grams) was precipitated as a straw colored powder. Crystallization from methanol and glacial acetic acid, in succession, afforded pale-yellow micro-crystals, m.p. 285-286° C. A suspension of this compound (2.18 grams) in a mixture of glacial acetic acid (120 ml) and azeotropic hydrobromic acid (60 ml) was heated under reflux for 1 hours. The starting material had dissolved within two hours and the desired product, 3,8-dihydroxy-dibenzo-alpha-pyrone, crystallized out after 6 hours as light yellow powder (1.9 grams). Recrystallization of the product from glacial acetic acid gave pale-yellow needles, m.p. 360-362° C. The purity of the products was determined by HPLC, and $^1$H-NMR spectra.

Example 3

Chemical Synthesis of 3,3',8,8'-tetrahydroxy-9,9'-bis-dibenzo-α-pyrone

The DBP-Dimer

Methanolic solutions of 3,8-dihydroxydibenzo-α.-pyrone (102 mg) and phosphomolybdic acid (108 mg) were mixed and then adsorbed on silica gel (60-120 mesh, 1 gram). It was desiccated and the residue was charged on top of a chromatographic column (silica gel, 12 grams). The column was moistened with light petrol and kept overnight at room temperature (25° C.±5° C.). Elution of the column with ethyl acetate-toluene (10:90) separated as a yellowish-orange layer. The solvent was evaporated and the residue, an amorphous yellowish-orange powder (41 mg), was collected. A further crop (7 mg) was obtained by eluting the column with aqueous-acetone. DBPs on autooxidation are converted into a yet stable bioactive product, the dimer (structure V, FIG. 1) as established by analytical (HPTLC) and spectroscopic (UV, IR, MS) data.

Example 4

Purification of Dibenzopyrones from Natural Sources

Alternatively, 3-hydroxy DBP, 3,8-dihydroxy DBP and dimeric DBPs can be isolated from Shilajit, ammonites etc., using generally known procedures (U.S. Pat. No. 6,869,612 to Ghosal).

Example 5

Chemical Synthesis of 3-O-glycinoyldibenzo-α-pyrone

Condensation of 3-hydroxydibenzo-α-pyrone with tert-butyloxycarbonyl (BOC) glycine (Aldrich), in presence of dicyclohexylcarbodiimide (DCC), produced 3-O-(BOC)-glycinoyldibenzo-α-pyrone. Deblocking of BOC, from the product, with trifluoroacetic acid, afforded 3-O-glycinoyl-dibenzo-α-pyrone (shilajit-dibenzo-α-pyrone chromoproteins of different origin all contain 3-O-glycinoyl-dibenzo-α-pyrone, thus the ubiquitous 3-hydroxydibenzo-α-pyrone conjugate).

Synthesis of other amino acyl analogs of DBPs can be obtained by substituting the appropriate amino acid in the above procedure.

Example 6

Isolation of DBPs from Animal Mitochondria

Mitochondria were isolated from heart and liver of chicken, goat and mice following a published procedure (Liu Y, Deng F, Zhao R and Qu S, *Chemosphere*, 40(8):851-854, 2000). Briefly, in a typical experiment, liver tissue from mice were triturated with sterilized medium comprising sucrose (Merck, 0.25 M), EDTA (Merck, 1 M), Tris-HCl (Merck, 10 mM), pH 7.4. The tissue was cut into small pieces, homogenized and centrifuged at 900 g for one minute. The supernatant was again centrifuged twice, for 20 minutes each time at 900 g. The sediment at each step was discarded. The clear supernatant was centrifuged twice at 12,000 g, 20 minutes each time, to form pellets of a mitochondria-enriched fraction. The fraction was divided into two parts. One part was resuspended in a measured volume of distilled water and sonicated (10 min×2). The mitochondrial suspension in water was centrifuged (12,000 g, 20 min) and the supernatant was collected and marked as 'mitochondrial water extract'. The other part of the mitochondria was similarly extracted with the Bligh and Dyer solvent system and the supernatant was marked 'mitochondrial B & D extract'. The two extracts were subjected to comprehensive HPTLC and HPLC analyses for detection and quantitation of DBPs and their equivalents.

The data from chicken and goat are as follows.

TABLE 1

Dibenzo-α-pyrones from Goat and Chicken

| Mitochondria isolated from liver of | 3-OH-DBP (ng/mg mitochondria enriched fraction) | 3,8-$(OH)_2$-DBP (ng/mg mitochondria enriched fraction) |
| --- | --- | --- |
| Goat | 80.00 | 10.00 |
| Chicken | 0.78 | 0.67 |

Example 7

Isolation of DBPs from Mitochondria of Swiss Albino Mice after Administration of DBPs Isolated from Shilajit and Comparison to Control Mice Administration (intra-peritoneally) of a 4:1 mixture of 3,8-$(OH)_2$-DBP and 3-OH-DBP (20 mg/Kg body weight) was carried out on Swiss Albino mice (20±2 g). One hour after administration the animals were sacrificed and mitochondria from liver were isolated and analyzed as described for Example 6.

HPTLC Conditions:
Stationary Phase—Silica Gel Aluminium sheet for TLC 60 $F_{254}$ (Merck)
Mobile Phase—Chloroform:Methanol 90:10
Sample application—CAMAG LINOMAT 5 (Automated applicator)
Detection—240 nm (CAMAG TLC SCANNER 3)
HPLC Conditions:
Column—NovaPak RP $C_{18}$ [150×3.9 mm]
Mobile phase—Acetonitrile:Water:o-Phosphoric acid 32:67:1
Flow Rate—1 ml/min
Detection—PDA 240 nm for DBPs
Detection of DBPs (free and conjugated forms) in mice mitochondria and increase in detected DBP subsequent to administration of exogenous DBPs 3-OH-DBP and 3,8-$(OH)_2$-DBP (and their conjugates) were detected in mitochondria of control mice by HPTLC. Administration of DBPs to the animals increased the amount of DBPs and its products in mitochondria as detected by using authentic markers of the two DBPs (Table 2).

TABLE 2

Amounts of DBP-products in mitochondria of mice liver before and after DBPs treatment, analyzed by HPTLC

| Product | Structure (as in FIG. 1) | $R_f$ | Amount (nmol/gm wet wt) in mitochondria before DBP treatment | Amount (nmol/gm wet wt) in mitochondria after DBP treatment |
| --- | --- | --- | --- | --- |
| 3,8-$(OH)_2$-DBP | II | 0.59 | 0.5 | 2.3 |
| 3,8-$(OH)_2$-DBP-semiquinone | III | 0.52 | 12.7 | 20.2 |
| 3,8-$(OH)_2$-DBP-quinone | IV | 0.43 | 26.7 | 24.8 |
| 3,8-$(OH)_2$-DBP-dimer | V | 0.28 | 22.9 | 28.6 |

Additionally, several other oxido-reductive products of DBPs were formed in the mitochondria of treated mice (Table 3).

TABLE 3

HPTLC data of oxido-reductive products of 3-OH-DBP and 3,8-(OH)$_2$-DBP produced in vivo

| Product | Structure (as in FIG. 1) | $R_f$ | Reflectance spectrum: $\lambda_{max}$ (nm) |
|---|---|---|---|
| 3-OH -DBP | I | 0.65 | 235, 277, 300, 335 |
| 3,8-(OH)$_2$-DBP | II | 0.59 | 220, 235, 280, 304, 355 |
| 3,8-(OH)$_2$-DBP-semiquinone | III | 0.52 | 225, 238, 280, 304, 336, 357, 370 |
| 3,8-(OH)$_2$-DBP-quinone | IV | 0.43 | 234, 286 |

When 3,8-(OH)$_2$-DBP is oxidized with either dilute hydrogen peroxide or ubiquinone, an unsymmetrical 3-line spectrum was produced (ESR spectra), in each case, with coupling constants of 1.45-1.48 G. The three equally-spaced lines of the triplet indicated interaction of the unpaired electron (semiquinone radical of DBP) with two equivalent ortho-protons. This might also be the sequence of formation of semiquinone radical and quinone of 3,8-(OH)$_2$-DBP in mitochondria, as oxidation by oxygen centered free radicals are conceivable in mitochondria.

Example 8

Figure 2:
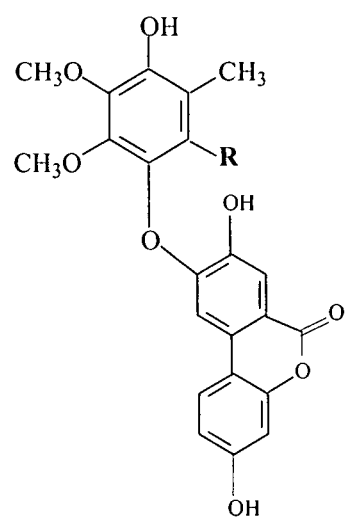
FIG. 2 $CoQ_{10}$-DBP conjugate; one canonical form wherein R is ten isoprene units.

Augmentation of CoQ$_{10}$ (or its Conjugates) in Rat (Stressed) Blood Plasma and Different Organs of Mice when Co-Administered Orally with 3,8-(Oh)$_2$-DBP One year old caged stressed Sprague-Dawley rats (250-270 gms) were fed the following, individually or in combination after suspension in 0.8% carboxymethyl cellulose: CoQ$_{10}$ (5 mg/Kg b.w./day) and 3,8-(OH)$_2$-DBP (5 mg/Kg b.w./day) for 5 days. Blood was collected by puncture of the retro-orbital plexus. The plasma was separated by centrifugation, extracted with methanol and subjected to HPLC. In another experiment, Swiss albino mice (20±2 g) were fed orally with—(a) 3,8-(OH)$_2$-DBP; (b) CoQ$_{10}$; (c) a combination of 3,8-(OH)$_2$-DBP and CoQ$_{10}$ and (d) 3,8-(OH)$_2$-DBP and CoQ$_{10}$ in a clathrated form with Shilajit-fusoms (each 5 mg/Kg b.w.), per day, for 5 days. The animals were subjected to hypoxic stress for 1 hour each day for 3 days from the 3rd day of the experiment. After the stipulated time-period, the content of CoQ$_{10}$ and their conjugates with DBP were estimated in heart, kidney, liver (in wet weight basis) and in blood, by HPLC, after proper extraction from the tissues according to the procedure depicted in the literature (Rousseau, G and Varin, F, Determination of Ubiquinone-9 and 10 levels in rat tissues and blood by High Performance Liquid Chromatography with Ultraviolet detection. *J. Chromat. Sci.*, 36(5): 247-252, 1998).
HPLC Conditions:
Column—RP C$_{18}$ Xterra [250×4 mm]
Mobile phase—Methanol:Acetonitrile:Ethanol 30:30:40
Flow rate—1 ml/min
Detection—PDA 275 nm for CoQ$_{10}$
In the blood plasma of chronic-stressed rats, the characteristic DBP-CoQ conjugates were absent as revealed in HPLC, by the absence of signals in the $t_R$ zone of 8 to 15 minutes. In lieu of that, several polar aberrant metabolites of CoQ$_{10}$ appeared in the $t_R$ zone 3 to 6 minutes. Since CoQH$_2$ is the active electron donor in electron transport chain, systemic balance of the two redox forms (CoQ$_{10}$☐CoQH$_2$) is needed. It seems that stress affected these animals and transformed all the CoQ into aberrant metabolites, in absence of the systemic antioxidants, notably, DBPs. Administration of CoQ$_{10}$ led to appearance of DBP-CoQ conjugates (characterized from the HPLC-PDA spectra), conceivably by the stabilization of the reduced form of the administered CoQ$_{10}$ with systemic DBPs by spin-pairing and formation of conjugates (FIG. 2). Another significant observation was that, co-administration of 3,8-(OH)$_2$-DBP with CoQ$_{10}$ (1:1 w/w ratio) significantly increased the amount of the conjugates (ca. 80% in average over the amount when only CoQ$_{10}$ was administered) in plasma of treated animals in comparison to the amounts present when CoQ$_{10}$ was administered singly (Table 4).

TABLE 4

Increment in the amounts of three DBP-CoQ conjugates in blood plasma of rats when 3,8-(OH)$_2$-DBP was co-administered with CoQ$_{10}$, analyzed by HPLC

| DBP-CoQ conjugate ($t_R$ in minute) | Increment in percent on administration of CoQ$_{10}$ along with 3,8-(OH)$_2$-DBP |
|---|---|
| 10.34 | 18.19 |
| 11.48 | 173.36 |
| 14.1 | 67.17 |

(These characteristic DBP-CoQ conjugates (ca. 0.03 nmol/ml) were also found in the blood plasma of healthy human volunteers of different age-groups (40-70 years), thereby indicating the importance of these conjugates in the mitochondrial CoQ functions). The chemical nature of these constituents ($t_R$ 10-14 minutes, Table 4) was determined by interaction of CoQ$_{10}$ and 3,8-(OH)$_2$-DBP in vitro. In methanol-acetonitrile-ethanol solvent (the HPLC mobile phase), these two compounds interacted to produce the oxido-reductive components and conjugates (cf. str. VII, FIG. 2). Thus, the above observations demonstrate that co-administration of 3,8-(OH)$_2$-DBP and CoQ$_{10}$, as oral nutritional supplement or topical personal care product, especially as a concentrated supplement or product could improve their concentrations in blood significantly in case of systemic deficiency (i.e. stress) thereby restoring systemic energy synthesis.

TABLE 5

Increment of coenzyme Q in normal mice blood plasma and organs [FSCD = clathrated complex of coenzyme Q$_{10}$ and 3,8-(OH)$_2$-DBP with fulvic acid system]

| | Coenzyme Q: | | | |
|---|---|---|---|---|
| Treatment | Blood (nmol/ml) | Heart (nmol/gm) | Liver (nmol/gm) | Kidney (nmol/gm) |
| Vehicle (control) | 0.79 | 18.46 | 15.38 | 11.86 |
| CoQ$_{10}$ | 0.81 | 35.69 | 19.41 | 16.51 |
| CoQ$_{10}$ + DBP | 0.82 | 36.99 | 25.03 | 17.81 |
| FSCD | 1.32 | 45.50 | 34.08 | 22.99 |

Bioavailability was more when CoQ$_{10}$ and 3,8-(OH)$_2$-DBP using the fulvic acid system. A systemic increment of CoQ$_{10}$ was also observed in mice plasma and a few organs upon oral feeding of this formulation. The extent of the increment of CoQ$_{10}$ was more when CoQ$_{10}$ and 3,8-(OH)$_2$-DBP were targeted to mitochondria using the fulvic acid delivery system (Table 5). A similar trend in the increment was also observed in the case of $CoQ_{10}$-DBP conjugates when the fulvic acid system was used. These findings demonstrate that $CoQ_{10}$ and 3,8-$(OH)_2$-DBP act in concert as a potent in vivo antioxidant. Thus, concurrent supplementation of $CoQ_{10}$ and 3,8-$(OH)_2$-DBP [or 3-OH-DBP, which is systemically converted into 3,8-$(OH)_2$-DBP] using a fulvic acid delivery system would efficiently perform their targeting to mitochondria. This can be regarded as effective therapeutic strategy against stress-induced oxidative damage of cells and DNA damage due to old-age.

Example 9

Stability of Reduced $CoQ_{10}$ ($CoQH_2$) by 3,8-$(OH)_2$-DBP at Different pH

Two mg of solid $CoQ_{10}$ (SRL, India), in an airtight vial was dissolved in 1 ml of methanol. After thorough vortexing, 5 mg of solid $NaBH_4$ (Merck India) was added, 1 mg at a time, to the yellow colored solution of $CoQ_{10}$ in methanol and kept in an ice-bath for a few minutes. The vial was kept shut to avoid contact with air but opened occasionally to avoid generation of pressure inside due to accumulation of hydrogen. After the reduction reaction, a clear colorless solution was obtained to which methanolic solution of 3,8-$(OH)_2$-DBP with a concentration of 1 mg/ml (>90% pure) was added in a ratio of 1:1 to obtain a final concentration of the mixture—reduced $CoQ_{10}$ mg/ml and DBP 0.5 mg/ml. This solution was analyzed by HPLC for reduced $CoQ_{10}$ content at different time intervals. A control was prepared in similar fashion except that no DBP was added. The pH of the solutions was determined to be 8 using pH paper. To obtain solutions of reduced $CoQ_{10}$ with pH 7 and pH 3, aliquots of concentrated HCl were added to the methanolic solution of reduced $CoQ_{10}$ at pH 8. Afterwards, a solution of DBP was added and analysis by HPLC at different time intervals was conducted, as before.

HPLC Conditions:

Column—NovaPak RP $C_{18}$ [150×3.9 mm]

Mobile phase—Methanol:Acetonitrile:Ethanol 30:30:40

Flow rate—1 ml/mil

Detection—PDA 290 nm for reduced $CoQ_{10}$

Stability of Reduced $CoQ_{10}$ ($CoQH_2$) by 3,8-$(OH)_2$-DBP at Different pH:

3,8-$(OH)_2$-DBP significantly protects reduced $CoQ_{10}$, in the pH range 3 to 8, from oxidative degradation (Tables 6-8).

TABLE 6

Stability of reduced $CoQ_{10}$ in absence and presence of 3,8-$(OH)_2$-DBP at pH 8

| Time (in min) | Reduced $CoQ_{10}$ remaining in control (%) | Reduced $CoQ_{10}$ remaining in presence of DBP (%) |
|---|---|---|
| 0 | 100.00 | 100.00 |
| 40 | 79.18 | 93.44 |
| 60 | 54.09 | 80.21 |
| 80 | 33.17 | 66.57 |
| 100 | 20.87 | 51.85 |

TABLE 7

Stability of reduced $CoQ_{10}$ in absence and presence of 3,8-$(OH)_2$-DBP at pH 7

| Time (in hour) | Reduced $CoQ_{10}$ remaining in control (%) | Reduced $CoQ_{10}$ remaining in presence of DBP (%) |
|---|---|---|
| 0 | 100.00 | 100.00 |
| 48 | 7.73 | 10.79 |
| 72 | 3.70 | 6.33 |

TABLE 8

Stability of reduced $CoQ_{10}$ in absence and presence of 3,8-$(OH)_2$-DBP at pH 3

| Time (in hour) | Reduced $CoQ_{10}$ remaining in control (%) | Reduced $CoQ_{10}$ remaining in presence of DBP (%) |
|---|---|---|
| 0 | 100.00 | 100.00 |
| 48 | 57.25 | 79.27 |
| 72 | 61.95 | 73.91 |

3,8-$(OH)_2$-DBP appears not to convert $CoQ_{10}$ to its totally reduced form, preservation of the reduced form of the coenzyme seems to have been mediated by the DBP-semiquinone radical. It is known that $CoQ_{10}$ functions in the electron transport chain by accepting electrons, forming a semiquinone and thereby passing the electron to ETC (Electron Transport Chain) complexes. In the present experiment, DBP-semiquinone radical produced from DBP, after donating an electron to NAD, stabilizes the $CoQ_{10}$ semiquinone radical by spin-pairing (FIG. 2). In a physiological system, DBP-semiquinone radical might conjugate with the CoQ-semiquinone radical thereby driving the reaction towards formation of reduced $CoQ_{10}$, which is essential in the electron transport chain. This was also reflected in the retarded autoxidation of reduced $CoQ_{10}$ in the presence of 3,8-$(OH)_2$-DBP (Table 9).

TABLE 9

Retarded autoxidation of $CoQH_2$ in presence of 3,8-$(OH)_2$-DBP at pH 8

| Time (in min) | Regenerated $CoQ_{10}$ in absence of 3,8-$(OH)_2$-DBP (μg/ml) | Regenerated $CoQ_{10}$ in presence of 3,8-$(OH)_2$-DBP (μg/ml) |
|---|---|---|
| 0 | 0 | 0 |
| 20 | 5.49 | 10.63 |
| 40 | 72.98 | 37.37 |
| 60 | 184.68 | 99.55 |
| 80 | 202.28 | 151.28 |
| 100 | 109.23 | 202.31 |

It has also been observed that regenerated $CoQ_{10}$ tended to form aberrant metabolites after 100 minutes of reaction, as its concentration decreased, in the absence of 3,8-$(OH)_2$-DBP (Table 9). 3,8-$(OH)_2$-DBP prevented such aberrant agglomeration of $CoQ_{10}$. The observation is highly significant because it lends credence to the fact that 3,8-$(OH)_2$-DBP preserves the integrity of $CoQ_{10}$ so that the coenzyme will not be degraded by potential systemic dysfunction.

Example 10

Inhibition of CoQ-CoQH$_2$ Aberrant Metabolite Formation During Red-Ox Recycling

Methanolic solution of coenzyme Q$_{10}$ (1 mg/ml) was reduced by NaBH$_4$ to pH 8 when the yellow solution became colorless. About 1 mg of 3,8-(OH)$_2$-DBP was added to the solution and the mixture was analyzed by HPLC at different time intervals (0-80 min). A control CoQ$_{10}$, without 3,8-(OH)$_2$-DBP, was prepared similarly and analyzed at different time intervals (0-80 min).

HPLC Conditions:
Column—NovaPak RP C$_{18}$ [250×4 mm]
Mobile phase—Methanol:Acetonitrile:Ethanol 30:30:40
Flow rate—1 ml/min
Detection—PDA 275 nm for CoQ$_{10}$ Inhibition of CoQ-CoQH$_2$ Aberrant Metabolite Formation During Redox Recycling:

Reduced CoQ$_{10}$ (CoQH$_2$) has a tendency to rapidly autoxidize in the presence of air. As seen from the HPLC chromatogram of the CoQH$_2$ solution, during autoxidation of CoQH$_2$ in vitro, several aberrant metabolites (t$_R$ zone 3 to 6 min) were formed. The aberrant metabolites increased rapidly with time (Table 10).

TABLE 10

Inhibition of aberrant metabolite formation of CoQ$_{10}$-CoQH$_2$ in vitro by DBF

| Time (in minutes) | Relative percentage of aberrant metabolites in absence of 3,8-(OH)$_2$-DBP | Relative percentage of aberrant metabolites in presence of 3,8-(OH)$_2$-DBP |
|---|---|---|
| 0 | 0 | 0 |
| 40 | 93% | 0 |
| 80 | 96% | 0 |

However, CoQH$_2$ in the presence of 3,8-(OH)$_2$-DBP did not form any aberrant metabolite for a long time. It seems that 3,8-(OH)$_2$-DBP performs the role of smooth electron transfer from CoQH$_2$ (to oxygen/cytochrome c) and inhibits the destruction of it. In other words, 3,8-(OH)$_2$-DBP maintains the prolonged red-ox reaction between CoQH$_2$ and CoQ$_{10}$. Thus, co-administration of 3,8-(OH)$_2$-DBP and CoQ$_{10}$ ensure the efficient energy generation in the mitochondria of recipients.

Example 11

Development of an In Vitro Model for the In Vivo Stability of NAD$^+$/NADH Ratio for Optimum Efficiency of the Electron Transport Chain

NAD (0.5 mg) was added to a methanolic solution of 3,8-(OH)$_2$-DBP (0.5 mg). The mixture was sonicated for 15 minutes and the product was subjected to HPLC analysis.

HPLC Conditions:
Column—NovaPak RP C$_{18}$ [250×4 mm]
Mobile phase—100 mM phosphate buffer [pH 6.00]
Flow rate—0.6 ml/min
Detection—PDA 260 nm for NAD and 340 nm for NAD-DBP conjugate NAD$^+$ shows $\lambda_{max}$ at 261.9 nm; t$_R$ 5.95 min; NAD$^+$-DBP conjugate, t$_R$ 5.95 min shows $\lambda_{max}$ 261.9 nm and 337 nm (due to reduced NAD$^+$ component) with additional maxima at $\lambda_{max}$ 271.4 nm, 347.5 nm and 379.6 nm (due to the DBP-chromophore).

Figure 3:
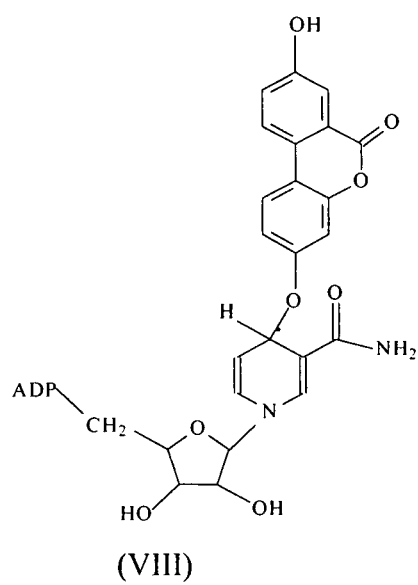
FIG. 3 Structure of NAD-dibenzo-α-pyrone conjugate.

This observation indicates that 3,8-(OH)$_2$-DBP can function as antioxidant in mitochondria thereby protecting NAD for utilization as energy currency. A systemic NAD:NADH ratio of 3 to 10 must be maintained in mammals for proper functioning of the electron transport chain (Swierczynski J, Slominska E, Smolenski R T and Mayer D, *Pol. J. Pharmacol.*, 53:125-130, 2001). Until the present investigation, the occurrence of oxygenated dibenzo-α-pyrones [e.g. 3,8-(OH)$_2$-DBP and equivalents] and their functions in the animal mitochondria were not known. It has now been shown that the NAD-DBP conjugate (FIG. 3, structure VIII) plays a central role in the mitochondrial electron transport chain. In support, nucleophilic addition product (comparable to structure VIII in FIG. 3) is well documented in the reaction: NAD$^+$+Nu$^-$.

Example 12

Targeting of CoQ$_{10}$ and 3,8-(OH)$_2$-DBP as Clathrated Fusom Complex to Tissues Thereby Protecting the Tissues from Stress-Induced Lipid Peroxidation

Swiss albino mice (20±g) were fed orally with—(a) 3,8-(OH)$_2$-DBP; (b) CoQ$_{10}$; (c) a combination of 3,8-(OH)$_2$-DBP and CoQ$_{10}$ and (d) 3,8-(OH)$_2$-DBP and CoQ$_{10}$ in a clathrated form with fusoms (each 5 mg/Kg b.w.), per day, for 5 days. The animals were subjected to hypoxic stress for 1 hour each day for 3 days from the 3$^{rd}$ day of the experiment. After the stipulated time-period, brain and liver of the animals were collected and mitochondria from the liver were separated as described previously (Liu Y, Deng F, Zhao R and Qu S, *Chemosphere*, 40(8):851-854, 2000). Lipid peroxidation in brain and liver-mitochondria was estimated by the method of Ohkawa et al. (Ohkawa H, Ohishi N and Yagi K, Assay for lipid peroxides in animal tissues by thiobarbituric acid reaction. *Anal. Biochem.*, 95:351-358, 1979).

Concurrent systemic administration of CoQ$_{10}$ and 3,8-(OH)$_2$-DBP protects brain tissues from stress-induced lipid peroxidation (Table 11). The purpose of the study was to determine whether supplemental intake of CoQ$_{10}$ and 3,8-(OH)$_2$-DBP alone or in combination, could protect/reduce brain tissues from the adverse effects of stress-induced lipid peroxidation. However, lowering of lipid peroxidation in brain was significantly prominent when both 3,8-(OH)$_2$-DBP and CoQ$_{10}$ were administered to mice orally in a fulvic acid system (Table 11). Lipid peroxidation in the mitochondria-enriched fraction (from liver) was also lowered when 3,8-(OH)$_2$-DBP was co-administered with CoQ$_{10}$.

TABLE 11

Effect of 3,8-(OH)$_2$-DBP, coenzyme Q$_{10}$ and combinations thereof on stress-induced lipid peroxidation of mouse brain.

| | Control | CoQ$_{10}$ | CoQ$_{10}$ + DBP | DBP | CoQ$_{10}$ + DBP + Fulvic acid |
|---|---|---|---|---|---|
| OD Values at 532 nm | 1.169 | 1.147 | 1.128 | 1.119 | 1.042 |

The lowering of lipid peroxidation was significant when both 3,8-$(OH)_2$-DBP and $CoQ_{10}$ were administered to mice orally in a fulvic acid system, (Table 12).

TABLE 12

Effect of 3,8-$(OH)_2$-DBP, coenzyme $Q_{10}$ and combinations thereof on stress-induced lipid peroxidation of mouse liver mitochondria.

|  | Control | $CoQ_{10}$ | $CoQ_{10}$ + DBP | DBP | $CoQ_{10}$ + DBP + Fulvic acid |
|---|---|---|---|---|---|
| OD Values at 532 nm | 0.495 | 0.467 | 0.412 | 0.395 | 0.321 |

The above observations indicate that $CoQ_{10}$ and 3,8-$(OH)_2$-DBP act in concert to reduce the adverse effect of reactive oxygen species-mediated tissue-injury, probably by increasing the bioavailability of both in the injury-afflicted tissues.

Example 13

Estimation of $CoQ_{10}$ and 3,8-$(OH)_2$-DBP in Humans of Different Age Groups

Human blood samples were taken from individuals in different age groups and $CoQ_{10}$ was estimated by HPLC according to the method of Rousseau et al. (Rousseau, G and Varin, F, Determination of Ubiquinone-9 and 10 levels in rat tissues and blood by High Performance Liquid Chromatography with Ultraviolet detection. *J. Chromat. Sci.*, 36(5):247-252, 1998). Estimation of 3,8-$(OH)_2$-DBP from human blood plasma was performed by precipitating the protein with methanol and analyzing the supernatant.

Depletion of Coenzyme $Q_{10}$ and DBPs in Humans Upon Aging:

Depletion of coenzyme $Q_{10}$ with aging and/or mitochondrial diseases is well established. [Kalen, A., Appelkvist, E. L., Daliner, G., *Lipids*, 24:579-584]. One of the reasons behind the fact might be the radical-induced peroxidation of mitochondrial membrane, leading to formation of aberrant CoQ-metabolites. Table 13 shows decline in the level of $CoQ_{10}$ with age [Molina J A, de Bustos F, Ortiz S, Del Ser T, Seijo M, Benito Leon J, Oliva J M and Perez, S, *J. Neural Transmission*, 109: 1195-1201, 2002; Watts G F, Castelluccio C, Rice-Evans C, Taub N A, Baum H and Quinn P J, *J. Clinical Pathology*, 46:1055-1057, 1993; Lagendijk J, Ubbink W J and Hayward Vermaak W J, *J. lipid Research*, 37:67-75, 1996); 3,8-$(OH)_2$-DBP also declines with age (present invention) (Table 13). In view of the above-mentioned observations, replenishment of both [$CoQ_{10}$ and 3,8-$(OH)_2$-DBP] for mitochondrial repair mechanism is necessary.

TABLE 13

Plasma coenzyme $Q_{10}$ and 3,8-$(OH)_2$-DBP levels in different age groups of normal human volunteers

| Groups | Coenzyme $Q_{10}$ (μg/l)[1] | 3,8-$(OH)_2$-DBP (μg/l) |
|---|---|---|
| 20-40 years | 1726.8 ± 215.75 (n = 5) | 6.94 ± 0.9 (n = 20) |
| 41-65 years | 897.9 ± 302 (n = 40) | 4.25 ± 0.66 (n = 9) |

[1]Values from the literature.

The mechanisms delineated in the present study of the oxido-reductase reactions, operating in the electron transport chain of animal mitochondria to generate ATP, point to a persuasive role of concurrent application of oxygenated dibenzo-α-pyrones (DBPs), viz. 3,8-$(OH)_2$-DBP (and equivalents) and coenzyme $Q_{10}$ ($CoQ_{10}$) in animals and humans. Further, to restore the age-related depreciation in the systemic concentration of DBPs in humans (Table 13), it would be logical to administer DBPs, from exogenous sources (such as, obtained synthetically or obtained from suitable natural sources, namely, Shilajit, ammonites etc.) along with $CoQ_{10}$ and, to make them readily bioavailable, to use an appropriate bioactive carrier, e.g. oligomeric DBPs (obtained from shilajit, ammonites etc. or prepared synthetically). Overall, the invention demonstrates, that concurrent supplementation of oxygenated DBPs and $CoQ_{10}$, by using oligomeric DBPs as the delivery system would be more effective than $CoQ_{10}$ alone as a potential remedial measure for age-related mitochondrial dysfunctions. The use of $CoQ_{10}$ in the management of age-related mitochondrial dysfunction has precedence in the literature. (F. L. Crane, Biochemical functions of coenzyme $Q_{10}$, *J. Am. College of Nutrition*, 20(6):591-598, 2001).

Example 14

Systemic ATP Regeneration by the DBPs in Mouse Engaged in Forced Swimming

Swiss albino mice (20±2 g) were fed orally with—(a) 3,8-$(OH)_2$-DBP and (b) 3-OH-DBP (each 25 mg/Kg b.w.), per day, for 7 days. In case of the controls, only vehicle (0.8% carboxymethyl cellulose in water) was administered for seven days of the experiment. The animals were subjected to 'forced swimming' for 30 minutes on the $7^{th}$ day of the experiment [Pliakas, A. M., Carlson, R. R., Neve, R. L., Konradi, C., Nestler, E. J. and Carlezon, W. A. 2001. *J. Neurosci.*, 21(18), 7397-7403]. Immediately after the swimming, blood was collected from all the animals for analysis of ATP and related nucleotides by HPLC [Smolenska, Z., Kaznowska, Z., Zarowny, D., Simmonds, H. A. and Smolenski, R. T. 1999. *Rheumatology*, 38, 997-1002; Komarova, S. V., Mosharov, E. V., Vitvitsky, V. M. and Ataullakhanov, F. I. 1999. *Blood Cell Mol. Dis.*, 25(13), 170-179; Marquardt, D. L., Gruber, H. E. and Wasserman, S. I. 1984. *Proc. Natl. Acad. Sci.*, 81, 6192-6196]. AEC (adenylate energy charge) was calculated according to the method of Atkinson and Walton [Atkinson D E & Walton G M, Adenosine triphosphate conservation in metabolic regulation, *J Biol Chem*, 242 (1967) 3239] and TAN (total adenine nucleotides) was calculated according to an established method [Spencer M K & Katz A, Role of glycogen in control of glycolysis and IMP formation in human muscle during exercise, *Am J Physiol*, 260 (1991) E859].

TABLE 14

Blood levels of ATP and energy related indices in albino mice treated with test compounds after forced swimming stress [Data represent mean ± standard error of the mean (SEM) of 6 animals]

| Test item treatment | ATP ($\mu$M) | AEC | TAN ($\mu$M) | ATP/ADP ratio |
|---|---|---|---|---|
| Control (Vehicle) | 0.60 ± 0.01 | 0.86 ± 0.003 | 0.79 ± 0.01 | 3.84 ± 0.09 |
| 3-hydroxydibenzo-α-pyrone (25 mg/Kg, p.o.) | 0.72 ± 0.03* | 0.89 ± 0.002* | 0.90 ± 0.04 | 4.82 ± 0.09* |
| 3,8-dihydroxydibenzo-α-pyrone (25 mg/Kg, p.o.) | 0.68 ± 0.03 | 0.88 ± 0.003* | 0.86 ± 0.03 | 4.30 ± 0.12 |

[*p < 0.05 compared to control (One-way ANOVA followed by Dunnett's Post Hoc Test)]

Example 15

Systemic ATP Regeneration by DBPs in Mice Exposed to Restraint Stress

Swiss albino mice (20±2 g) were fed orally with—(a) 3-OH-DBP and (b) 3,8-(OH)$_2$-DBP (each 25 mg/Kg b.w. per day, for 7 days). In case of the controls, only vehicle (0.8% carboxymethyl cellulose in water) was administered for seven days of the experiment. All the animals of all the groups were subjected to restraint stress (for 60 minutes) on the seventh day of the experiment, 2 hours after drug administration, according to a published method [Figueiredo, H. F., Bodie, B. L., Tauchi, M., Dolgas, C. M. and Herman, J. P. 2003. *Endocrinology*, 144, 5249-5258]. The model was selected in the present experiment, because restraint stress is a widely used model of acute oxidative stress. Immediately after being exposed to stress, the animals were sacrificed, blood was collected for analysis by HPLC of ATP and related nucleotides [Smolenska, Z., Kaznowska, Z., Zarowny, D., Simmonds, H. A. and Smolenski, R. T. 1999. *Rheumatology*, 38, 997-1002; Komarova, S. V., Mosharov, E. V., Vitvitsky, V. M. and Ataullakhanov, F. I. 1999. *Blood Cell Mol. Dis.*, 25(13), 170-179; Marquardt, D. L., Gruber, H. E. and Wasserman, S. I. 1984. *Proc. Natl. Acad. Sci.*, 81, 6192-6196], and liver was collected for measurement of superoxide dismutase and catalase activities [Zielinski, S, and Pörtner, H. 2000. *Comparative Biochem. Physiol*. Part B, 125, 147-[60]. AEC (adenylate energy charge) was calculated according to the method of Atkinson and Walton [Atkinson D E & Walton G M, Adenosine triphosphate conservation in metabolic regulation, *J Biol Chem*, 242 (1967) 3239] and TAN (total adenine nucleotides) was calculated according to an established method [Spencer M K & Katz A, Role of glycogen in control of glycolysis and IMP formation in human muscle during exercise, *Am J Physiol*, 260 (1991) E859].

TABLE 15

Blood levels of ATP and energy related indices in albino mice treated with test compounds after exposure to restraint stress [Data represent mean ± standard error of the mean (SEM) of 6 animals]

| Test item treatment | ATP ($\mu$M) | ADP ($\mu$M) | AEC | TAN ($\mu$M) | ATP/ADP ratio |
|---|---|---|---|---|---|
| Control (Vehicle) | 0.67 ± 0.03 | 0.14 ± 0.02 | 0.89 ± 0.01 | 0.76 ± 0.03 | 4.90 ± 0.32 |
| 3-hydroxydibenzo-α-pyrone (25 mg/Kg, p.o.) | 0.66 ± 0.04 | 0.09 ± 0.01 | 0.90 ± 0.01 | 0.79 ± 0.05 | 7.04 ± 0.38* |
| 3,8-dihydroxydibenzo-α-pyrone (25 mg/Kg, p.o.) | 0.64 ± 0.05 | 0.09 ± 0.01 | 0.90 ± 0.01 | 0.76 ± 0.06 | 6.96 ± 0.49* |

[*p < 0.01 compared to control (One-way ANOVA followed by Dunnett's Post Hoc Test)]

Oxygenated dibenzo-α-pyrones (viz. 3-hydroxydibenzo-t-pyrone and 3,8-dihydroxydibenzo-α-pyrone), DBPs, are the key components of ReVitalET™, a purified Shilajit product, which are responsible for the rejuvenating action. Of the two oxygenated dibenzo-α-pyrones (DBPs) present in ReVitalET™, 3-hydroxydibenzo-α-pyrone [3-OH-DBP] was found to work better in protecting animal organisms from different forms of oxidative stress. 3-OH-DBP significantly improved content of ATP, AEC values and ATP/ADP ratio (in blood) in albino mice engaged in forced swimming. The other oxygenated DBPs, viz. 3,8-dihydroxydibenzo-α-pyrone [3,8-(OH)$_2$-DBP] showed significant improvement only in some parameters following the same experimental protocol. Significant improvement was also observed in the ATP/ADP ratio (in blood) of the DBPs-treated animals in the restraint stress model, with indications of improvement also in the other parameters. All these findings indicated that 3-OH-DBP is important for physiological homeostasis in animal organisms, probably via formation of 3,8-dihydroxydibenzo-α-pyrone and a probable further oxidatioii/hydroxylation to a tri-hydroxylated common metabolite in situ.

Superoxide radical scavenging activities in the liver of animals, treated with each of the three test compounds (Table 16) also showed augmentation of radical captodative function. This result substantiates the earlier findings on the antioxidant capacities of the DBPs [Ghosal, S. 2006. *Shilajit in Perspective*, Narosa-Alpha Science Intl., New-Delhi-Oxford). However, catalase activities in liver remained unaltered (Table 17). These observations suggest that the DBPs scavenge superoxide radicals by intercepting them into the aryl nuclei producing polyoxygenated/polymeric DBPs. The above findings further indicate that 3-hydroxydibenzo-α-pyrone contributes to physiological homeostasis in animal organisms by capturing reactive oxygen radicals (ROS).

TABLE 16

Superoxide dismutase (SOD) activity in liver of albino mice treated after exposure to restraint stress

|  | Control | 3-OH-DBP | 3,8-di DBP |
|---|---|---|---|
| SOD activity in liver (U/gm tissue) | 0.6 | 0.91 | 0.98 |

TABLE 17

Catalase activity in liver of albino mice treated after exposure to restraint stress

|  | Control | 3-OH-DBP | 3,8-di DBP |
|---|---|---|---|
| Catalase activity in liver (U/mg tissue) | 3.9 | 3.5 | 3.4 |

Personal Care and Cosmetic Formulations

Example 16

Anhydrous System with Sunscreens

| INCI NAME | % |
|---|---|
| Phase A | |
| Beeswax | 9.00 |
| Ozokerite | 5.00 |
| Cyclomethicone | 36.00 |
| Cyclomethicone (and) Dimethicone Crosspolymer | 37.00 |
| Phase B | |
| Bismuth Oxychloride | 1.00 |
| Phase C | |
| Homosalate | 7.00 |
| Avobenzone | 2.00 |
| Coenzyme $Q_{10}$ | 0.50 |
| 3,8-dihydroxy-dibenzo-α-pyrone | 0.50 |
| Total | 100.00 |

Procedure: Blend ingredients in Phase A; heat with mixing until clear and uniform. Blend bismuth oxychloride into Phase A. Blend ingredients in Phase C separately; apply heat if needed. Cool Phase A to 60-65° C. and add Phase C with mixing. When the mixture is uniform it may be packaged.

Example 17

Anhydrous delivery system with antioxidants

| INCI NAME | % |
|---|---|
| Phase A | |
| Beeswax | 9.00 |
| Ozokerite | 5.00 |
| Cyclomethicone | 35.00 |
| Cyclomethicone (and) Dimethicone Crosspolymer | 40.00 |
| Phase B | |
| Cyclomethicone | 3.50 |
| Cyclomethicone (and) Dimethicone Crosspolymer | 5.50 |
| Emblica antioxidant | 1.00 |
| Coenzyme $Q_{10}$ | 0.50 |
| 3,8-dihydroxy-dibenzo-α-pyrone | 0.50 |
| Total | 100.00 |

Procedure: Blend ingredients in Phase A; heat with mixing at about 70<80° C. until clear and uniform. Blend ingredients in Phase B separately at a temperature below 60° C., e.g. room temperature; the mixture should be smooth and contain no lumps. Cool Phase A to about 60° C. and add Phase B with mixing. When the mixture is uniform it may be packaged.

Example 18

Anti-Aging Moisturizing Lotion

| INCI NAME | % w/w |
|---|---|
| Phase A-1 | |
| Water (demineralized) | 55.65 |
| Disodium EDTA | 0.05 |
| Propylene Glycol | 5.00 |
| Phase A-2 | |
| Xantham Gum | 0.20 |
| Phase B | |
| PEG-6 stearate, ceteth-20, glyceryl stearate, steareth-20, stearic acid | 10.00 |
| Stearic Acid | 1.00 |
| Hydrogenated castor oil | 1.00 |
| Octyldodecyl myristate | 8.00 |
| Dimethicone | 4.00 |
| Phenyltrimethicone | 2.00 |
| Sweet Almond oil | 3.00 |
| Coenzyme $Q_{10}$ | 0.50 |
| Purified Shilajit | 1.00 |
| Phase C | |
| Water (demineralized) | 5.00 |
| *Phyllanthus emblica* fruit extract | 0.50 |
| Niacinamide | 2.00 |
| Phase D | |
| Triethanolamine | 0.10 |
| Phase E | |
| Phenoxyethanol, Isopropylparaben, Isobutylparaben, Butylparaben | 1.00 |
| Total | 100.00 |

Procedure: Disperse A-2 in A-1 and heat to 70-75° C. Combine B and heat to 70-75° C. Add B to A while stirring. Homogenize until mixture cools to 60° C. At 30° C. add phase C. Adjust pH with TEA to 5.0-6.0. Add phase E. Mix until uniform.

Example 19

| Skin Rejuvenating (O/W) Lotion | |
|---|---|
| INCI NAME | % W/W |
| Phase A | |
| Polyglyceryl-3 Methyl Glucose Distearate | 3.50 |
| Glyceryl stearate | |
| PEG-100 stearate | 2.50 |
| Dicapryl ether | 5.00 |
| Coco-caprylate/caprate | 5.00 |
| Propylene Glycol Dicaprylate/Dicaprate | 3.00 |
| Almond oil | 2.00 |
| Cetyl alcohol | 1.50 |
| Coenzyme $Q_{10}$ | 0.50 |
| 3,8-dihydroxy-dibenzo-α-pyrone or Shilajit | 0.50 |

| Skin Rejuvenating (O/W) Lotion | |
|---|---|
| INCI NAME | % W/W |
| Phase B | |
| Glycerine | 3.00 |
| Propylene glycol | 3.00 |
| Allantoin | 0.20 |
| Methylparaben | 0.15 |
| Water | qs |
| Phase C | |
| Phenoxyethanol and Isopropylparaben and isobutyl paraben and butylparaben | 0.50 |
| Total | 100 |

Procedure: Combine A, stir and heat to 65° C. Combine B, stir and heat to 65° C. Add A to B while stirring. Homogenize at moderate speeds to avoid foaming, while allowing mixture temperature to cool to 40° C. Add C, homogenize. Stir gently until mixture is homogeneous.

Example 20

| Skin Lightening Lotion with Anti-Aging Benefits | | |
|---|---|---|
| INCI NAME | TRADE NAME | % w/w |
| Phase A | | |
| Water (demineralized) | | 69.30 |
| Disodium EDTA | | 0.05 |
| Methyl Gluceth-10 | Glucam E-10 | 1.00 |
| Phase B | | |
| Butylene Glycol | | 5.00 |
| Xantham Gum | Vanzan NF | 0.20 |
| Sclerotium Gum | Amigel | 0.70 |
| Phase C | | |
| Cetearyl alcohol and cetearyl glucoside | Montanov 68 | 6.00 |
| Lecithin | Yelkin SS | 0.20 |
| Dicaprylyl Carbonate | Cetiol CC | 3.00 |
| Cetyl Alcohol | | 0.50 |
| Dimethicone | Dow Corning 200 Fluid 10 cst | 0.70 |
| Coenzyme $Q_{10}$ | Present invention | 0.50 |
| 3,8-dihydroxy-dibenzo-α-pyrone | Present invention | 0.50 |
| Phase D | | |
| Water (demineralized) | | 10.00 |
| *Phyllanthus emblica* fruit extract | Emblica | 1.00 |
| Phase E | | |
| Triethanolamine | TEA 99% | 0.15 |
| Phase F | | |
| Phenoxyethanol, Isopropylparaben, Isobutylparaben, Butylparaben | Liquapar PE | 1.00 |
| Phase G | | |
| Fragrance | "Orange Blossom" # 832 513 | 0.10 |
| Total | | 100.00 |

Procedure: Combine A and heat to 70-75° C. Disperse B in A. Combine C and heat to 70-75° C. Add C to A/B while stirring. Homogenize until mixture cools to 60° C. At 40° C. add D. Adjust pH with TEA to 4.0-4.5 with E. Add F. Add G. Mix until mixture reaches RT.

Pharmaceutical, Nutritional & Veterinary Formulations

Example 21

Capsules with Health-Restorative and Health Promotional Benefits

| Ingredient | Per Capsule, g |
|---|---|
| Coenzyme $Q_{10}$ and 3,8-dihydroxy DBP (1:1) | 0.200 |
| Microcrystalline Cellulose | 0.150 |
| Syloid (Fumed Silicon Dioxide) | 0.005 |
| Croscarmellose Sodium | 0.010 |
| Stearic Acid | 0.010 |
| Size 0 Empty Gelatin Capsule | 0.100 |
| TOTAL | 0.475 |

Procedure:
1. Blend Coenzyme $Q_{10}$ and 3,8-dihydroxy DBP (1:1), Microcrystalline Cellulose, Croscarmellose Sodium and Syloid (screened through 30 mesh) in a suitable blender for 15 minutes.
2. Screen Stearic Acid through a 30 mesh, add to the above blender and mix for 5 minutes.
3. Fill into capsules with a target fill weight of 0.375 g.
4. Polish the capsules.

Example 22

Extra Strength Capsules with Health-Restorative and Health Promotional Benefits

| Ingredient | Per Capsule, g |
|---|---|
| Coenzyme $Q_{10}$ and 3,8-dihydroxy DBP (1:1) | 0.500 |
| Microcrystalline Cellulose | 0.150 |
| Syloid (Fumed Silicon Dioxide) | 0.005 |
| Croscarmellose Sodium | 0.010 |
| Stearic Acid | 0.010 |
| Size 00 Empty Gelatin Capsule | 0.120 |
| TOTAL | 0.795 |

Procedure:
1. Blend Coenzyme $Q_{10}$ and 3,8-dihydroxy DBP (1:1), Microcrystalline Cellulose, Croscarmellose Sodium and Syloid (screened through 30 mesh) in a suitable blender for 15 minutes.
2. Screen Stearic Acid through a 30 mesh, add to the above blender and mix for 5 minutes.
3. Fill into capsules with a target fill weight of 0.675 g.
4. Polish the capsules.

Example 23

Tablets with Health-Restorative and Health Promotional Benefits

| Ingredient | Per Tablet, g |
|---|---|
| Coenzyme $Q_{10}$ | 0.100 |
| Purified Shilajit | 0.100 |
| Microcrystalline Cellulose | 0.150 |
| Syloid (Fumed Silicon Dioxide) | 0.005 |
| Croscarmellose Sodium | 0.010 |
| Stearic Acid | 0.010 |
| TOTAL | 0.500 |

Procedure:
1. Blend Coenzyme $Q_{10}$ and purified Shilajit, Microcrystalline Cellulose, Croscarmellose Sodium and Syloid (screened through 30 mesh) in a suitable blender for 15 minutes.
2. Screen Stearic Acid through a 30 mesh, add to the above blender and mix for 5 minutes.
3. Compress into tablets with a target weight of 0.375 g.
4. Coat the tablets if necessary.

Example 24

Tablets with Health-Restorative and Health Promotional Benefits

| Ingredient | Per Tablet, g |
|---|---|
| Coenzyme $Q_{10}$ and 3,8-dihydroxy DBP or 3-hydroxy DBP (1:1) | 0.100 |
| Microcrystalline Cellulose | 0.550 |
| Syloid (Fumed Silicon Dioxide) | 0.005 |
| Croscarmellose Sodium | 0.010 |
| Stearic Acid | 0.010 |
| TOTAL | 0.675 |

Procedure:
1 Blend Coenzyme $Q_{10}$ and 3,8-dihydroxy DBP or 3-hydroxy DBP (1:1), Microcrystalline Cellulose, Croscarmellose Sodium and Syloid (screened through 30 mesh) in a suitable blender for 15 minutes.
2 Screen Stearic Acid through a 30 mesh, add to the above blender and mix for 5 minutes.
3. Compress into tablets with a target weight of 0.675 g.
4. Coat the tablets if necessary.

Example 25

Chewable Tablets with Health-Restorative and Health Promotional Benefits

| Ingredient | Per Tablet, g |
|---|---|
| Coenzyme $Q_{10}$ and purified shilajit (1:1)Taste-masked, 33% | 0.379 |
| Sodium ascorbate | 0.098 |
| Microcrystalline Cellulose | 0.050 |
| Sodium Saccharin Powder | 0.002 |
| Compressible Sugar | 0.100 |

-continued

| Ingredient | Per Tablet, g |
|---|---|
| Stearic Acid | 0.012 |
| Imitation Orange Flavor | 0.002 |
| FD&C Yellow #6 Dye | 0.001 |
| Fumed Silicon Dioxide (#30 mesh) | 0.006 |
| TOTAL | 0.650 |

Procedure:
1. Blend all the ingredients, except Stearic Acid, in a suitable blender for 15 minutes.
2. Screen steraic Acid through a 30 mesh and blend with the above blend for 5 minutes.
3. Compress into tablets with a target weight of 0.650 g.

Example 26

Oral Suspension with Anti-Obesity, Health-Restorative and Health Promotional Benefits

| Ingredient | % |
|---|---|
| Coenzyme $Q_{10}$ and 3,8-dihydroxy DBP (1:1) | 2.50 |
| Colloidal magnesium aluminum silicate premix (5% formula 21) | 20.00 |
| Polaxamer 331 | 0.05 |
| Glycerin | 10.00 |
| Potassium sorbate | 0.20 |
| Sodium benzoate | 0.10 |
| Color | Qs |
| Flavor | Qs |
| Liquid sugar | 67.15 |
| Citric acid or Sodium hydroxide to pH 5.5 | Qs |
| Purified water, qs | 100.0 |

Procedure:
1. Dissolve potassium sorbate, sodium benzoate and color in glycerin.
2. Add liquid sugar, colloidal magnesium aluminum silicate premix and half of the polaxamer 331 with agitation.
3. Disperse the rest of the polaxamer 331 and Safed Musli extract with agitation.
4. Add flavor and pass the suspension through a colloid mill or a homogenizer rinsing thoroughly with purified water.
5. Adjust pH to 5.5 with either Citric acid or Sodium hydroxide solution.
6. Add purified water to make the final volume and mix well.

Example 27

Maintenance B-Complex Vitamin Tablets or Capsules with Health-Restorative and Health Promotional Benefits

| Ingredient | Per Tablet/Capsule, mg |
|---|---|
| Coenzyme $Q_{10}$ and 3,8-dihydroxy DBP (1:1) | 50.00 |
| Vitamin A acetate (dry from 500 IU) | 11.00 |
| Thiamini mononitrate, USP | 1.65 |
| Riboflavin, USP | 2.10 |
| Pyridoxine HCl, USP | 2.10 |
| Cyanocobalamine, 1% | 4.50 |
| D-Calcium pantothenate, USP | 7.50 |
| Niacinamide, USP | 22.00 |
| Dicalcium phosphate dihydrate, USP | 26.20 |
| Microcrystalline cellulose, NF | 61.95 |
| Talc, USP | 6.00 |
| Stearic acid, NF | 3.00 |
| Magnesium stearate, NF | 2.00 |
| TOTAL | 200.00 |

Procedure:
1. Blend all the ingredients, except Stearic acid and Magnesium stearate, in a suitable blender for 15 minutes.
2. Add Stearic acid and Magnesium stearate and blend for 5 minutes.
3. Compress into 200 mg tablets or fill into capsules with a target fill weight of 200 mg.

Example 28

| Sugar Free Iced Tea Powdered Soft Drink Mix | |
|---|---|
| Ingredients | % |
| Tea Powder | 48.68 |
| $CoQ_{10}$ and 3,8-dihydroxy benzophenone | 2.00 |
| Tween 80 | 5.00 |
| Citric Acid | 27.83 |
| Maltodextrin, M100 | 9.28 |
| NutraSweet ® brand Sweetener | 6.03 |
| Flavors % Colors | 1.18 |
| TOTAL | 100.0 |

Procedure: Process: Mix all the powdered ingredients in a suitable blender for 15 minutes.
Serving Size: 1.3 g mixed with 8 oz of water Example 29

| Ready to Drink Beverages (30% Orange Juice Beverage) | |
|---|---|
| Ingredient | % |
| Treated Water | qs |
| Citric Acid | 0.170 |
| NutraSweet ® brand Sweetener | 0.040 |
| $CoQ_{10}$ + Shilajit (1:1) | 0.500 |
| Solubilizer | 1.00 |
| Potassium citrate | 0.020 |
| Orange juice concentrate | 5.620 |
| Orange flavor | 0.090 |
| Peach Flavor | 0.490 |
| Color (1% solution) | 0.200 |
| TOTAL | 100.00 |

Procedure: Blend water with Citric acid, solubilizer and present inventive composition under agitation. Add the sweetener and mix well until the sweetener dissolves. Add other ingredients and mix thoroughly. Pasteurize as normal plant practice. Cool and pack.
Serving Size: 8 oz

Example 30

| Meal Replacement Beverage Mix (Chocolate flavored meal) | |
| --- | --- |
| Ingredient | % |
| Sucrose | 39.00 |
| Whey protein concentrate, 34% | 18.50 |
| Dutch processed Cocoa, 16-18% fat | 11.50 |
| Corn syrup solids | 11.50 |
| Sodium caseinate | 11.00 |
| $CoQ_{10}$ and Shilajit | 0.50 |
| Calcium caseinate | 5.00 |
| Vitamin/Mineral Premix (Adjusted to provide 25-30% of daily recommended intake based on 2000 kcal diet) | 1.00 |
| Vanilla extract | 0.90 |
| Lecithin | 0.80 |
| Xanthan gum | 0.20 |
| Carboxy Methyl Cellulose | 0.10 |
| TOTAL | 100.0 |

Procedure: Dry blend all the ingredients and package as desired. To serve, mix 40 g of the dry mixture in 225 ml of milk.

Example 31

| Sports Beverage for increased energy | |
| --- | --- |
| Ingredient | % |
| Purified Water | 76.68 |
| Maltodextrin, 18DE | 10.00 |
| Fructose | 9.15 |
| 80% Whey protein concentrate (WPC80) | 3.60 |
| Coenzyme $Q_{10}$ and purified Shilajit or oligomeric 3,8-dihydroxy-dibenzo-1-pyrone (1:2) | 0.15 |
| Citric Acid | 0.56 |
| Flavor | 0.09 |
| Sodium citrate dihydrate | 0.06 |
| Color | 0.01 |
| TOTAL | 100.0 |

Procedure: Add water to a large mixing tank at 15-25° C. With good agitation, add WPC80, avoiding entrapment of air. Allow mixture to sit for 15-30 minutes so that WPC80 can become hydrated. Mix in fructose, maltodextrin, sodium citrate and present inventive composition with good agitation. Add flavor and color. Allow to hydrate for 10 minutes Adjust pH to 3.5-3.7 using a 50% solution of an appropriate acid while continuously mixing. Hot-fill containers. Cool beverages immediately.
Serving Size: 220 g

Example 32

| Energizing Instant Coffee | |
| --- | --- |
| Anti-Stress Instant Coffee | |
| Ingredient | % |
| Ingredient | % |
| Instant Coffee | 96.00 |
| $CoQ_{10}$ and Shilajit (0.5:1) | 4.00 |
| Solubilizer | qs |
| TOTAL | 100.0 |

Procedure: Mix present inventive composition with solubilizer and Coffee extract until thoroughly mixed. Instantise by freeze-drying or another appropriate method. Pack into bottles or aluminum pouches.
Serving Size: 5 gm mixed in 200 ml hot water

Example 33

| Energy bar | |
| --- | --- |
| Ingredient | % |
| Brown Rice Syrup | 21.10 |
| Brown Rice Crisp Cereal | 14.10 |
| Old Fashioned Rolled Oats | 10.60 |
| Quick Rolled Oats | 10.60 |
| Water | 10.60 |
| Dried Cherries | 8.80 |
| Cherry-Flavored Dried Cranberries | 7.10 |
| Plum Paste | 6.50 |
| Whey Protein Isolate | 4.80 |
| $CoQ_{10}$ + purified Shilajit (0.25:1.0) | 1.00 |
| Unsalted Butter | 3.40 |
| Glycerin | 0.80 |
| Black Cherry Flavor | 0.50 |
| Sodium Bicarbonate | 0.10 |
| TOTAL | 100.0 |

Procedure: Combine the first ten ingredients, except water, in the bowl of a large mixer. Mix on low speed for 2 minutes. Add butter, black cherry flavor and glycerin and mix on low speed for 1 minute. Add water and mix on low speed for 1½ minutes. Sheet bars to 11 mm thickness and cut into 1½"× 1½" pieces. Place on parchment lined pans so that they are not touching each other. Bake at 204° C. for 7 minutes.
Serving Size: 50 g

Example 34

Granulation Suitable for Compression into Tablets, Filling into Capsules, and Dispersion into a Drink, Etc

| S. No | INGREDIENT | AMOUNT PER UNIT DOSE, mg | AMOUNT PER BATCH, g |
| --- | --- | --- | --- |
| 1 | Polysorbate 80 | 7.500 | 3.0 |
| 2 | Purified Water | — | 200.0 |
| 3 | Coenzyme $Q_{10}$ | 50.000 | 20.0 |
| 4 | Purified Shilajit | 50.000 | 20.0 |
| 5 | Microcrystalline Cellulose, NF, 101 | 50.000 | 20.0 |

Procedure:

| 1 | Heat water to about 50 degrees C. |
| --- | --- |
| 2 | Add Polysorbate 80 and mix well. |
| 3 | Add Coenzyme $Q_{10}$ to the mixture in Step 3 and mix for 30 minutes in a sonicating bath at about 50 degrees C. using a homogenizing mixer. |
| 4 | Add Shilajit and continue mixing for another 30 min. |
| 5 | Add Microcrystalline Cellulose and mix for 10 min. |
| 6 | Dry the dispersion in an oven at about 50 degrees for 12 hours. |
| 7 | Pass the dried granulation through 40 mesh screen by hand or through a FitzMill using slow speed, knives forward and 30 mesh screen. |

Example 35

Granulation Suitable for Compression into Tablets, Filling into Capsules, and Dispersion into a Drink, Etc

| S. No | INGREDIENT | AMOUNT PER UNIT DOSE, mg | AMOUNT PER BATCH, g |
|---|---|---|---|
| 1 | Purified Water | — | 200.0 |
| 2 | Coenzyme $Q_{10}$ | 50.000 | 20.0 |
| 3 | Purified Shilajit | 50.000 | 20.0 |
| 4 | Microcrystalline Cellulose, NF, 101 | 50.000 | 20.0 |

Procedure:

| 1 | Heat water to about 50 degrees C. in a sonicating bath. |
|---|---|
| 2 | Add Shilajit and mix for 30 minutes using a homogenizing mixer under sonication. |
| 3 | Add Coenzyme $Q_{10}$ to the mixture in Step 2 and mix for 30 minutes. |
| 4 | Add Microcrystalline Cellulose and mix for 10 min. |
| 5 | Dry the dispersion in an oven at about 50 degrees for 12 hours. |
| 6 | Pass the dried granulation through 40 mesh screen by hand or through a FitzMill using slow speed, knives forward and 30 mesh screen. |
| 7 | Blend the granulation from Step 6 with processing aids such as a disintegrant, glidant, lubricant, etc. and compress into tablets or fill into capsules. |
| 8 | Alternatively, the granulation from Step 6 can be directly dissolved in water, milk, etc. to make a drink. |

Example 36

Granulation Suitable for Compression into Tablets, Filling into Capsules, and Dispersion into a Drink, Etc

| S. No | INGREDIENT | AMOUNT PER UNIT DOSE, mg | AMOUNT PER BATCH, g |
|---|---|---|---|
| 1 | Sosium Lauryl Sulfate | 7.500 | 3.0 |
| 2 | Purified Water | — | 200.0 |
| 3 | Coenzyme $Q_{10}$ | 50.000 | 20.0 |
| 4 | Purified Shilajit | 50.000 | 20.0 |
| 5 | Microcrystalline Cellulose, NF, 101 | 50.000 | 20.0 |

Procedure:

| 1 | Heat water to about 50 degrees C. |
|---|---|
| 2 | Add Sodium Lauryl Sulfate and mix with a homogenizing mixer under sonication for 10 minutes. |
| 3 | Add Coenzyme $Q_{10}$ to the mixture in Step 2 and mix for 30 minutes. |
| 4 | Add Shilajit and continue mixing for another 30 min. |
| 5 | Add Microcrystalline Cellulose and mix for 10 min. |
| 6 | Dry the dispersion in an oven at about 50 degrees for 12 hours. |
| 7 | Pass the dried granulation through 40 mesh screen by hand or through a FitzMill using slow speed, knives forward and 30 mesh screen. |
| 8 | Blend the granulation from Step 7 with processing aids such as a disintegrant, glidant, lubricant, etc. and compress into tablets or fill into capsules. |
| 9 | Alternatively, the granulation from Step 7 can be directly dissolved in water, milk, etc. to make a drink. |

The preceding examples are instructive to obtain similar success by substituting the generically or specifically described reactants and/or operating conditions of this invention for those used in the preceding examples.

The entire disclosure of all applications, patents and publications, cited above are hereby incorporated by reference.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. A method of treating a mitochondrial disorder comprising administering to a subject suffering from a mitochondrial disorder a composition comprising purified (a) Coenzyme $Q_{10}$ (Co$Q_{10}$), reduced Co$Q_{10}$, or mixtures thereof, and (b) oxygenated dibenzo-α-pyrone or an amino acyl ester thereof wherein the composition is orally administered to an adult at least 5 mg per day of the composition and 3-OS-DBP is systemically converted to 3,8(OH)$_2$-DBP.

2. The method of claim 1, wherein the composition additionally contains a solubilizer capable of solubilizing Coenzyme $Q_{10}$ in water.

3. The method of claim 1, wherein the composition additionally comprises a carrier, delivery system, diluent or excipient that is acceptable for pharmaceutical, nutritional, cosmetic or veterinary usage.

4. The method of claim 3, wherein the carrier or delivery system is fulvic acid derived from 3,8-dihydroxy dibenzo-α-pyrone.

5. The method of claim 4, wherein the fulvic acid is obtained from purified Shilajit.

6. The method of claim 3, wherein said delivery system comprises oligomeric oxygenated dibenzo-α-pyrone.

* * * * *

UNITED STATES PATENT AND TRADEMARK OFFICE
CERTIFICATE OF CORRECTION

PATENT NO. : 8,894,993 B2
APPLICATION NO. : 11/881630
DATED : November 25, 2014
INVENTOR(S) : Shibnath Ghosal Page 1 of 1

It is certified that error appears in the above-identified patent and that said Letters Patent is hereby corrected as shown below:

In the Claims

Claim 15 should read:
A method of treating a mitochondrial disorder comprising administering to a subject suffering from a mitochondrial disorder a composition comprising purified (a) Coenzyme Q10 (CoQ10), reduced CoQ10, or mixtures thereof, and (b) oxygenated dibenzo-a-pyrone or an amino acyl ester thereof wherein the composition is orally administered to an adult at least 5 mg per day of the composition and 3-OH-DBP is systemically converted to 3,8(0H)rDBP.

Not:
A method of treating a mitochondrial disorder comprising administering to a subject suffering from a mitochondrial disorder a composition comprising purified (a) Coenzyme Q10 (CoQ10), reduced CoQ10, or mixtures thereof, and (b) oxygenated dibenzo-a-pyrone or an amino acyl ester thereof wherein the composition is orally administered to an adult at least 5 mg per day of the composition and 3-OS-DBP is systemically converted to 3,8(0H)rDBP.

Signed and Sealed this
Twentieth Day of August, 2019

Andrei Iancu
*Director of the United States Patent and Trademark Office*

UNITED STATES PATENT AND TRADEMARK OFFICE
CERTIFICATE OF CORRECTION

PATENT NO. : 8,894,993 B2  Page 1 of 1
APPLICATION NO. : 11/881630
DATED : November 25, 2014
INVENTOR(S) : Shibnath Ghosal It is certified that error appears in the above-identified patent and that said Letters Patent is hereby corrected as shown below:

In the Claims

Claim 1 should read:
A method of treating a mitochondrial disorder comprising administering to a subject suffering from a mitochondrial disorder a composition comprising purified (a) Coenzyme Q10 (CoQ10), reduced CoQ10, or mixtures thereof, and (b) oxygenated dibenzo-a-pyrone or an amino acyl ester thereof wherein the composition is orally administered to an adult at least 5 mg per day of the composition and 3-OH-DBP is systemically converted to $3,8(OH)_2DBP$.

Not:
A method of treating a mitochondrial disorder comprising administering to a subject suffering from a mitochondrial disorder a composition comprising purified (a) Coenzyme Q10 (CoQ10), reduced CoQ10, or mixtures thereof, and (b) oxygenated dibenzo-a-pyrone or an amino acyl ester thereof wherein the composition is orally administered to an adult at least 5 mg per day of the composition and 3-OH-DBP is systemically converted to 3,8(0H)rDBP.

This certificate supersedes the Certificate of Correction issued August 20, 2019.

Signed and Sealed this
Thirty-first Day of March, 2020

Andrei Iancu
*Director of the United States Patent and Trademark Office*